United States Patent
Wood et al.

(10) Patent No.: US 8,614,205 B2
(45) Date of Patent: Dec. 24, 2013

(54) GLUTAMATE RECEPTOR MODULATORS AND THERAPEUTIC AGENTS

(76) Inventors: Richard D Wood, Washington Crossing, PA (US); William Welsh, Princeton, NJ (US)

( * ) Notice: Subject to any disclaimer, the term of this patent is extended or adjusted under 35 U.S.C. 154(b) by 0 days.

(21) Appl. No.: 13/507,097

(22) Filed: Jun. 2, 2012

(65) Prior Publication Data

US 2013/0150416 A1 Jun. 13, 2013

Related U.S. Application Data

(62) Division of application No. 12/381,086, filed on Mar. 6, 2009, now Pat. No. 8,211,882.

(51) Int. Cl.
*A01N 43/00* (2006.01)
*A61K 31/33* (2006.01)

(52) U.S. Cl.
USPC ........... 514/183; 514/371; 514/476; 514/423; 514/563; 514/622; 514/467

(58) Field of Classification Search
None
See application file for complete search history.

(56) References Cited

FOREIGN PATENT DOCUMENTS

EP 1512397 A1 * 3/2005

* cited by examiner

*Primary Examiner* — Brandon Fetterolf
*Assistant Examiner* — Jean Cornet
(74) *Attorney, Agent, or Firm* — Richard Wood

(57) ABSTRACT

The present invention discloses methods of modulating the activity of Group I mGluRs using a defined class of benzamide compounds. In one embodiment, methods of modulating the activity of mGluR1 are provided. In another embodiment, methods of modulating the activity of mGluR5 are provided. In still another embodiment, methods of simultaneously modulating the activities of both mGluR1 and mGluR5 are provided. The present invention also provides methods of treating diseases or disorders which are mediated in full or in part by Group I mGluRs using one or more compounds belonging to the defined class of benzamide compounds. The present invention further provides methods of preventing diseases or disorders which are mediated in full or in part by Group I mGluRs using one or more compounds belonging to the defined class of compounds.

5 Claims, 1 Drawing Sheet

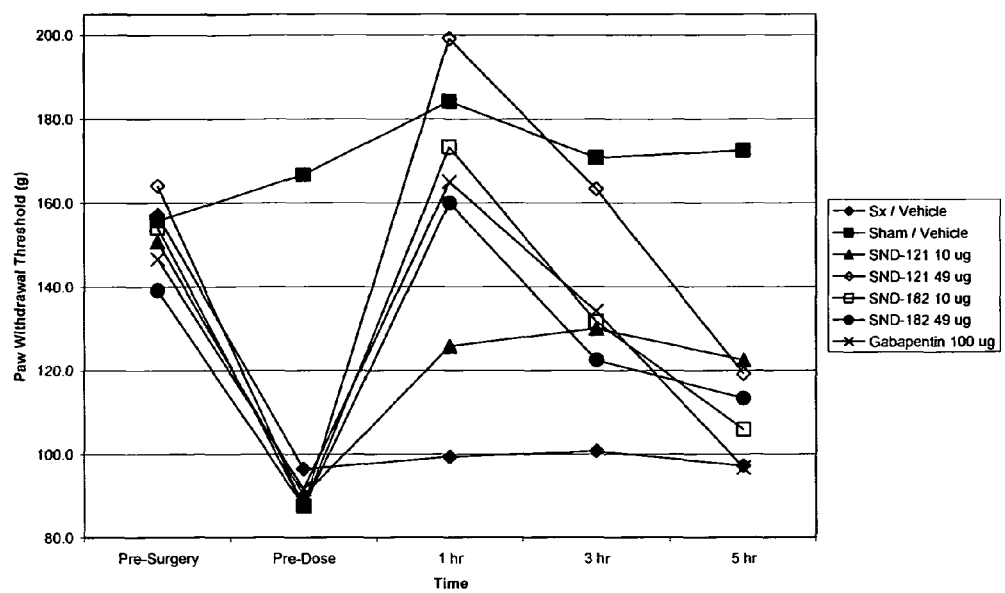
Partial Sciatic Nerve Efficacy Data SND-121 and SND-182
PSN/SND-121 is Compound 1; PSN/SND-182 is Compound 21; PSN/Vehicle is 9% DMSO/27% Cremophor/ 64% Saline

GLUTAMATE RECEPTOR MODULATORS AND THERAPEUTIC AGENTS

CROSS-REFERENCES TO RELATED APPLICATIONS

This application is a Divisional of application Ser. No. 12/381,086 filed Mar. 6, 2009 now U.S. Pat. No. 8,211,882.

FIELD OF THE INVENTION

The invention relates to compounds and methods to use compounds to treat diseases or disorders mediated in full or in part by Group 1 metabotropic glutamate receptors.

BACKGROUND OF THE INVENTION

The amino acid glutamate (L-glutamic acid) is recognized as the major excitatory neurotransmitter in the CNS. The excitatory amino acid receptors which respond to glutamate are of great physiological importance and play a key role in a variety of physiological processes such as long-term potentiation (learning and memory), the development of synaptic plasticity, motor control, respiratory and cardiovascular regulation, and sensory perception.

Excitatory amino acid receptors are classified into two general types and both are activated by glutamate and its analogs. Receptors activated by glutamate that are directly coupled to the opening of cation channels in the cell membrane of the neurons are termed ionotropic glutamate receptors (iGluRs). This type of receptor has been subdivided into three subtypes, which are defined by the depolarizing actions of the selective agonists N-Methyl-D-aspartate (NMDA), α-Amino-3-hydroxy-5-methylisoxazole-4-propionic acid (AMPA), and Kainic acid (KA).

The second general type of glutamate receptor belongs to the G-protein or second messenger-linked class of receptors and are known as "metabotropic" glutamate receptors (mGluRs). The metabotropic receptors are coupled to multiple second messenger systems that lead to enhanced phosphoinositide hydrolysis, activation of phospholipase D, increases or decreases in cyclic adenosine monophosphate (cAMP) formation, and changes in ion channel function (Schoepp D. et al, 1993; Trends in *Pharmacological Science* 14:13). Both types of receptors appear not only to mediate normal synaptic transmission along excitatory pathways but also to participate in the modification of synaptic connections during development and throughout life. Research has shown that mGluRs are implicated in a number of normal as well as pathological mechanisms in both the central nervous system and the periphery. Activation of neuronal mGluRs can influence levels of alertness, attention and cognition, protect nerve cells from excitotoxic damage resulting from ischemia, hypoglycemia and anoxia, modulate the level of neuronal excitation, influence central mechanisms involved in controlling movement, reduce sensitivity to pain, and reduce levels of anxiety.

Eight different types of the mGluRs have been identified: mGluR1-8 (Knopfel et al., 1995, *J. Med. Chem.*, 38, 1417-1426). These receptors function to modulate the presynaptic release of glutamate, and the postsynaptic sensitivity of neuronal cells to glutamate excitation. Based on pharmacology, sequence homology, and the signal transduction pathway that they activate, the mGluRs have been sub-classified into three groups. Group I consists of mGluR1 and mGluR5. They are coupled to hydrolysis of phosphatidylinositol (PI) and are selectively activated by (R,S)-3,5-dihydroxyphenylglycine (Brabet et al. 1995; *Neuropharmacology*, 34, 895-903). Group II consists of mGluR2 and mGluR3 receptors. They are negatively coupled to adenylate cyclase and are selectively activated by (2S,1'R,2'R,3'R)-2-(2,3-dicarboxycyclopropyl)glycine (DCG-IV; Hayashi et al. 1993; *Nature*, 366, 687-690). Group III consists of mGluR4, mGluR6, mGluR7 and mGluR8. They are also negatively coupled to adenylate cyclase and are selectively activated by (L)-2-amino-4-phosphonobutyric acid (L-AP4).

Antagonists which selectively bind to the mGluRs have been reported. Some phenylglycine derivatives, for example S-4CPG (S-4-carboxyphenylglycine), S-4C3HPG (S-4-carboxy-3-hydroxyphenylglycine) and S-MCPG (S-.alpha.-methyl-4-carboxyphenylglycine) have been reported to antagonize trans-ACPD-stimulated phosphoinositide hydrolysis and thus possibly act as antagonists at mGluR1 and mGluR5 subtypes (Thomsen, C. et al 1993; *Eur. J. Pharmacol.* 245: 299). More recently, compounds exhibiting selective agonist or antagonist activity at the mGluRs have been reported. Group I receptors (mGluR1 and mGluR5) play a key role in the central sensitization of pain, in addition to a variety of functions with potential implications in neurological and psychiatric disorders. (Schoepp, D. et al 1999; *Neuropharmacology* 38:1431-1476; Han, J. et al 2005; *Pain* 113:211-222.) A number of behavioral and electrophysiological studies have demonstrated a specific role for Group I mGluRs, and in particular mGluR1 receptors, in nociceptive processing in the CNS, including mechanisms of hyperalgesia and inflammation (Bhave, G. et al 2001; *Nat. Neurosci.* 4:417-423; Dolan, S. et al 2002; *Neuropharmacology* 43:319-326; Dolan, S. et al 2003; *Pain* 106:501-512; Young, M. et al 1994; *Neuropharmacology*, 33:141-144; Young, M. et al 1997; *Brain Res.* 777:161-169). The mGluR1-active compounds are also implicated in the treatment of pain. Antagonists at the Group 1 mGluRs antagonize sensory synaptic response to noxious stimuli of thalamic neurons (Eaton, S. A. et al. 1993; *Eur. J. Neuroscience*, 5:186). The intrinsic activation of spinal mGluR1 in chronic nociception has been demonstrated using antagonists, antibodies, and antisense oligonucleotides. Intrathecal administration of an mGluR1 antagonist produced antinociceptive effects in a formalin-induced model of nociceptive behavior (Neugebauer, V. 2001; *Trends Neurosci.* 24:550-552). There is mounting evidence to suggest that mGluR1 antagonists can be used for the treatment of chronic pain (Neugebauer, V. et al 2002; *Expert Opin. Ther. Targets* 6:349-361; Swanson, C. et al 2005; *Nat. Rev. Drug Discovery* 4:131-144). Several groups have reported a variety of structurally diverse non-competitive allosteric mGluR1 antagonists, such as LY456066 (Ambler, S. et at WO2001032632), JNJ16259685 (Mabire, D. et al 2005; *J. Med. Chem.*, 48:2134-2153), A-841720 (Zheng, G. et al 2005; *J. Med. Chem.* 48:7374-7388), and R214127 (Maibre et at WO 02/28837).

The use of compounds active at the mGluRs for the treatment of epilepsy was demonstrated by the influence of trans-ACPD on the formation of convulsions (Sacaan et al, *Neuroscience Lett.* 139, 77, 1992) and that phosphoinositide hydrolysis mediated via mGluR1 is increased after convulsion-causing stimulation experiments in rats (Akiyama et al. *Brain Res.* 569, 71, 1992). Trans-ACPD has been shown to increase the release of dopamine in the rat brain, which indicates that compounds acting on the mGluRs might be usable for the treatment of Parkinson's disease and Huntington's Chorea disease (Sacaan et al., *J. Neurochemistry* 59, 245, 1992).

Trans-ACPD has also been shown to be a neuroprotective agent in a medial cerebral artery occlusion (MCAO) model in mice (Chiamulera et al. 1992; *Eur. J. Pharmacol.* 216:335), and it has been shown to inhibit NMDA-induced neurotoxicity in nerve cell cultures (Koh, V. 1991, *Proc. Natl. Acad. Sci. USA* 88:9431).

Compounds active at the mGluRs for treatment of neurological diseases such as senile dementia have also been reported (Zheng, G. et al 1992; *Neuron* 9:163; Bashir et al 1993; *Nature* 363:347). These studies demonstrated that activation of mGluRs is necessary for the induction of long-term potentiation (LTP) in nerve cells of the septal nucleus and hippocampus. In addition it was shown that long-term depression (LTD) in nerve cells is induced after activation of mGluRs in cerebellar granule cells (Linden et al. 1991; *Neuron* 7:81). mGluRs may also be involved in addictive behavior, alcoholism, drug addiction, sensitization and drug withdrawal (Wickelgren, I. 1998; *Science*, 280:2045).

In addition to involvement in disorders of the central and peripheral nervous system, mGluRs have recently been implicated as contributing to the development of certain cancers. In recent years, glutamate signaling in cancer has been a focus of investigation. Studies have implicated the involvement of glutamate signaling in tumor development through mGluRs. The role of glutamate signaling in non-neuronal tissues is poorly understood, but studies have shown that a variety of G protein-coupled receptors and G proteins, including those that signal through phosphoinositide hydrolysis and cAMP accumulation, have been implicated in tumorigenesis through either mutational activation or overexpression (Dhanasekaran, N. et al, 1995; *Endocr. Rev.* 16:259-270; Gutkind, J. 1998; *Oncogene* 17:1331-1342.). Glutamate has recently been linked to tumor growth in both neuronal and non-neuronal cancers (Takano, T. et al. 2001; *Nat. Med.* 7:1010-1015; Rzeski, W. et al 2001; *Proc. Natl. Acad. Sci. USA* 98:6372-6377). Glutamate has been shown to stimulate proliferation of lung carcinoma cells in serum-deprived media, and antagonists of the ionotropic AMPA and NMDA glutamate receptors have been shown to inhibit proliferation and increase cell death in a calcium-dependent manner in a variety of non-neuronal cancers (Rzeski, W. et al 2001; supra). Agonist stimulation of mGluR5 in subconfluent melanocyte cultures has been shown to result in melanocytic proliferation (Frati, C. et al. 2000; *J. Cell. Physiol.* 183:364-372). It was recently shown that transgenic mice bred to be predisposed to develop multiple melanomas expressed an abundance of mGluR1 in melanoma cells but not in normal melanocytes, and that ectopic expression of mGluR1 was sufficient to cause melanoma (Pollack, P. et al 2003; *Nature Genetics* 34:108-112). The same study revealed that mGluR1 expression was detected in several human melanoma tumors and cell lines but not in benign nevi (clusters of melanocytes on the skin) or melanocytes. Several cell lines have been developed from independent mouse melanoma tumors (Marin, Y. et al 2005; *Neuropharmacol.* 49:70-79). These cell lines are useful tools in the studies of signaling events that may be mediated by mGluR1 in transformed melanocytes. In these cells, stimulation of mGluR1 by quisqualate, a Group I competitive glutamate receptor agonist, results in inositol triphosphate (IP3) accumulation, and the activation of the extracellular signal-related protein kinase 1/extracellular signal-related protein kinase 2 (ERK1/2) cell signaling pathway. The extracellular signal-regulated kinase (ERK) signaling pathway is a major determinant in the control of diverse cellular processes such as proliferation, survival, differentiation and motility. This pathway is often up-regulated in human tumors and as such represents an attractive target for the development of anticancer drugs. Because of its multiple roles in the acquisition of a complex malignant phenotype, specific blockade of the ERK pathway is expected to result in not only an antiproliferative effect but also in antimetastatic and antiangiogenic effects in tumor cells. IP3 accumulation and ERK1/2 activation were inhibited by pretreatment of the tumor cells with a mGluR1-specific antagonist (S-2-methyl-4-carboxy-phenylglycine, LY367385) or by dominant negative mutants of mGluR1, demonstrating that stimulation of mGluR1 initiates the ERK pathway but that this action may be inhibited by an antagonist. It was shown that ERK1/2 activation by mGluR1 was PKC-dependent, but cAMP and PKA-independent. These results suggest that mGluR1 and glutamate signaling may be used as novel targets for melanoma therapy (Nankoon et al, 2007 *Cancer Res.* 67:2298-2305).

Several diseases and disorders are mediated by improper functioning of glutamate receptors. Because excitatory amino acid receptors in general and mGluRs in particular are implicated in diverse normal physiological processes, there is a need to identify compounds capable of modulating receptor-mediated functions. For example, partial antagonism of mGluRs might be clinically useful in treating disorders wherein the process mediated by the receptor is pathologically enhanced. Partial antagonism might be clinically useful in treating disorders wherein the is an overabundance of the indigenous ligand stimulating the receptor to induce a critical function. There is a need to identify and develop methods of treatment and methods of prevention of disorders related to the improper functioning of mGluRs and specifically those in Group I.

BRIEF DESCRIPTION OF THE INVENTION

The present invention discloses methods of modulating the activity of Group I mGluRs using a defined class of compounds. Surprisingly, it was found that selected benzamide compounds modulated the activity of Group 1 mGluRs. In one embodiment, methods of modulating the activity of mGluR1 are provided. In another embodiment, methods of modulating the activity of mGluR5 are provided. In still another embodiment, methods of simultaneously modulating the activities of both mGluR1 and mGluR5 are provided. The present invention also provides methods of treating diseases or disorders which are mediated in full or in part by Group I mGluRs using one or more compounds belonging to the defined class of benzamide compounds. The present invention further provides methods of preventing diseases or disorders which are mediated in full or in part by Group I mGluRs using one or more compounds belonging to the defined class of benzamide compounds. Diseases and disorders contemplated include, but are not limited to, diseases and disorders of the central nervous system, the peripheral nervous system, the gastrointestinal system, the circulatory system, skin, retina, brain, heart, and lungs. It will be clear to those with skill in the art that the distribution and function of Group 1 mGluRs in animals is not completely understood, and that diseases or disorders in which Group 1 mGluRs are implicated, whether known at the present or unveiled in the future, are contemplated and are within the scope of the instant invention.

BRIEF DESCRIPTION OF THE DRAWING

FIG. 1 graphically portrays the ability of Compound 1 and Compound 21 to reverse hyperalgesia in the partial sciatic nerve ligation (PSN) model of neuropathic pain in the rat, as compared to gabapentin.

DETAILED DESCRIPTION OF THE INVENTION

The present invention provides methods of modulating the activity of Group I mGluRs, and preventing or treating diseases or disorders which are mediated by Group I mGluRs, comprising contacting the Group I mGluRs with one or more allosteric modulator of the invention in an amount sufficient to modulate the activity or prevent or treat the disease or disorder.

Antagonists and agonists of receptors which bind to and are active at only a particular receptor subtype are "selective" agents, whereas those which bind to and are active at more than one receptor subtype are "non-selective". "Orthosteric" ligands are agonists or antagonists which bind to and are active at the primary receptor binding site of a receptor, which is that portion of the receptor to which the endogenous neurotransmitter (glutamate) binds. Orthosteric agents therefore compete with the neurotransmitter for binding at the primary site, and may be further classified as "competitive" agonists or antagonists. Agonists or antagonists which bind to and are active at a secondary, and in some cases a tertiary, receptor binding site, which are spatially distinct domains for which the endogenous neurotransmitter has very little or no affinity, are termed "allosteric" ligands. These allosteric ligands are "non-competitive" in that, even in high concentration, they will not displace the endogenous ligand by competing for the primary binding site. However, compounds which bind to an allosteric site in a receptor may mitigate, modify, attenuate, enhance, diminish, inhibit, or prohibit the binding of the endogenous neurotransmitter or other orthosteric ligand to the primary binding site. Alternatively compounds which bind to an allosteric site in a receptor may mitigate, modify, attenuate, enhance, diminish, inhibit, or prohibit the physiological function of the activated receptor which include, among others, ion flux regulation, signaling, phosphorylation, and recruitment of proteins. The potency of attraction of an agonist or antagonist, whether orthosteric or allosteric, to its binding site in the receptor, is determined by the sum of non-covalent attractive and repulsive chemical forces of the ligand for the binding site, and is referred to as "affinity". A high affinity agonist or antagonist will bind to its respective site in the receptor at very low concentration, while much higher concentrations of low-affinity molecules are required before significant binding occurs. Agonists or antagonists with sufficient affinity to bind to an allosteric site will produce a dramatic change in the physiological function of an activated mGluR. Such agonists or antagonists are referred to herein as "allosteric modulators" and may exhibit positive (enhanced physiological function) or negative (diminished physiological function) modulation. An object of this invention is to provide selective allosteric modulators for the prevention and treatment of a disease or disorder which is associated with abnormal, aberrant, or excessive function of Group I mGluRs. A further object of this invention is to provide negative allosteric modulators of mGluR1, negative. allosteric modulators of mGluR5, and negative allosteric modulators of both mGluR1 and mGluR5.

According to the present invention, selective allosteric modulators with specificity for either mGluR1 or mGluR5 are provided. The mGlu1 and mGlu5 receptors exhibit different patterns of expression in the CNS, suggesting distinct functions for each receptor. mGluR5 receptors are expressed with high to moderate density in frontal cortex, caudate, putamen, nucleus accumbens, olfactory tubercle, hippocampus, and dorsal horn of the spinal cord, whereas low levels of expression are observed in the cerebellum. In contrast, mGluR1 receptor is expressed in high density in the cerebellum, but low to moderate expression is observed in frontal cortex, caudate, putamen, nucleus accumbens, and olfactory tubercle. Therefore it is understood that allosteric modulators selective for mGluR1 might produce physiological effects distinct from those produced by allosteric modulators selective for mGluR5.

Negative allosteric modulators with affinity for either mGluR1 or mGluR5 will produce effects at the receptor which may include the induction of a change in receptor conformation resulting in a diminished affinity of the endogenous ligand for the primary binding site, and decrease of physiologic function of the activated receptor. Such functional modulation may lead to decreased phosphoinositide hydrolysis, decreased mobilization of intracellular $Ca^{2+}$, and decreased activation of protein kinase C.

Conversely, positive allosteric modulators with affinity for either mGluR1 or mGluR5 might produce effects at the receptor which may include an enhancement of affinity of the endogenous ligand for the primary binding site or a subsequent enhancement of the normal physiologic function of the activated receptor.

The present invention is directed to methods of treating a disease or disorder which is mediated fully or in part by mGluR1 or mGluR5 using compounds of Formula I, and pharmaceutically acceptable salts, prodrugs, enantiomers, or hydrates thereof:

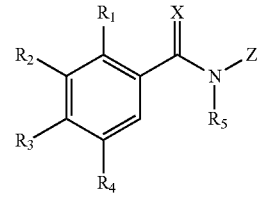

Formula I wherein
$R_1$=H, SH, or $OR_6$;
$R_2$ and $R_3$ are selected from fused phenyl, H, lower alkyl, I, Br, Cl, F, $CF_3$, $CH_2CF_3$, $CH_2Ph$, CH=$CH_2$, C≡CH, $OCH_3$, $OCF_3$, Ph, OPh, and $NO_2$;
$R_4$ is selected from the group consisting of H, lower alkyl, I, Br, Cl, F, $CF_3$, $CH_2CF_3$, $CH_2Ph$, CH=$CH_2$, C≡CH, C≡N, $OCH_3$, $OCF_3$, Ph, OPh, and $NO_2$;
$R_5$ is H, lower alkyl, or phenyl;
$R_6$ is selected from the group consisting of H, $COCH_3$, $COCH_2CH_3$, $COCH(CH_3)_2$, $COC(CH_3)_3$, COPh, $COCH_2Ph$, $COC_6H_4NO2(p)$, $COC_6H_4OH(p)$, $COC_6H_4NH_2(p)$, CON$(CH_3)_2$, CON$(CH_2CH_3)_2$, CON$(CH_3)(CH_2CH_3)$, CON$(CH_2Ph)_2$, CON$(CH_3)(CH_2Ph)$, 1-pyrrolidinecarbonyl, 2-carboxy-1-pyrrolidincarbonyl, (2S)-2-carboxy-1-pyrrolidinecarbonyl, (2R)-2-carboxy-1-pyrrolidinecarbonyl, 1-morpholinecarbonyl, 4-methyl-1-piperazinecarbonyl, sarcosine-N-carbonyl, CO-N-Me-Ala-OH, CO-N-Me-Val-OH, CO-N-Me-Leu-OH, CO-N-Me-Ile-OH, CO-N-Me-Val-OH, CO-N-Me-Met-OH, CO-N-Me-Phe-OH, CO-N-Me-Trp-OH, CO-Pro-OH, CO-N-Me-Gly-OH, CO-N-Me-Ser-OH, CO-N-Me-Thr-OH, CO-N-Me-Cys-OH, CO-N-Me-Tyr-OH, CO-N-Me-Asn-OH, CO-N-Me-Gln-OH, CO-N-Me-Asp-OH, CO-N-Me-Glu-OH, CO-N-Me-Lys-OH, CO-N-Me-Arg-OH, CO-N-Me-His-OH, CO-N-Me-Gly-Gly-OH, CO-N-Me-Gly-Phe-OH, CO-N-Me-Gly-Glu-OH, CO-N-Me-Gly-Glu-Glu-OH, CO-N-Me-Glu-Glu-OH, CO-N-Me-Gly-Lys-OH, CO-N-Me-Gly-Lys-Lys-OH, CO-Pro-Glu- OH, CO-Pro-Glu-Glu-OH, CO-Pro-Gly-OH, CO-Pro-Gly-Lys-OH, and CO-Pro-Lys-Lys-OH;

X is O or S; and

Z is substituted phenyl, or substituted 5- or 6-membered heterocyclic ring containing 1 or 2 heteroatoms chosen from N, O, and S, wherein said phenyl substituents are selected from the group consisting of H, lower alkyl, I, Br, Cl, F, $CF_3$, $CH_2CF_3$, $CH_2Ph$, $CHPh_2$, $CH=CH_2$, E-CH=CHCH$_3$, Z—CH=CHCH$_3$, C≡CH, C≡N, $OCH_3$, $OCF_3$, OPh, and $NO_2$ and wherein said heterocyclic ring substituents are selected from the group consisting of H, lower alkyl, I, Br, Cl, F, $CF_3$, $CH_2CF_3$, $CH_2Ph$, $CH=CH_2$, C≡CH, C≡N, $OCH_3$, $OCF_3$, Ph, OPh, and $NO_2$.

The term "pharmaceutically acceptable salts" refers to salts prepared from pharmaceutically acceptable non-toxic bases or acids including inorganic or organic bases and inorganic or organic acids. When the compound of the present invention is acidic, salts may be prepared from pharmaceutically acceptable non-toxic bases, including inorganic and organic bases. Salts derived from inorganic bases include aluminum, ammonium, calcium, copper, ferric, ferrous, lithium, magnesium, potassium, sodium, and zinc salts, and the like. Salts in the solid form may exist in more than one crystal structure, and may also be in the form of hydrates. Salts derived from pharmaceutically acceptable organic non-toxic bases include, but are not limited to, salts of primary amines, secondary amines, tertiary amines, substituted amines including naturally occurring substituted amines, cyclic amines, arginine, betaine, caffeine, choline, N,N'-dibenzylethylene-diamine, diethylamine, 2-diethylaminoethanol, 2-dimethylamino-ethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), orotic acid, caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, isethionic acid, lactic acid (DL), lactobionic acid, lauric acid, maleic acid, malic acid (L), malonic acid, mandelic acid (DL), methanesulfonic acid, mucic acid, naphthalene-1,5-disulfonic acid, naphthalene-2-sulfonic acid, nicotinic acid, nitric acid, oleic acid, oxalic acid, palmitic acid, pamoic acid, pantothenic acid, phosphoric acid, propionic acid, pyroglutamic acid (L), salicylic acid, sebacic acid, stearic acid, succinic acid, sulfuric acid, tartaric acid (L), thiocyanic acid, p-toluenesulfonic acid, and undecylenic acid. It will be understood that, as used herein, compounds of Formula I are meant to also include the pharmaceutically acceptable salts.

The term "fused phenyl" refers to an compound in which two of the carbon atoms of a benzene ring are shared in a larger structure. Non-limiting examples include 1-naphthol, in which a benzene ring can be visualized as fused at carbons 2 and 3 of phenol, and 1,2,3,4-tetrahydronaphthaline, which can be visualized as benzene fused to cyclohexene.

The term "radical" refers to a chemical array of atoms which is bonded to another atom in a compound of the invention. The radical is a domain of a molecule described herein, and is not intended to be understood as a separate chemical entity, but rather a substituent or substituent array of atoms which is a part of a molecule of the invention. A radical as used herein is not intended to be understood to have ionic charge or singlet or triplet character, but rather covalently bonded to another domain of the compound of the invention. Stylistic depictions of radicals herein are intended solely to illustrate certain embodiments of the invention.

The term "lower alkyl" means straight-chain or branched hydrocarbon radicals containing 6 or fewer carbons. Examples include, but are not limited to, methyl, ethyl, propyl, butyl, isopropyl, and tert-butyl, signified by $CH_3$, $CH_2CH_3$, $CH_2CH_2CH_3$, $(CH_2)_3CH_3$, $CH(CH_3)_2$, and $C(CH_3)_3$, respectively. Further examples include cyclopropyl, cyclobutyl, cyclopentyl, and cyclohexyl.

The term "$EC_{50}$" refers to the concentration of test compound or agonist at which response is halfway between baseline and maximum. Likewise, "$EC_{80}$" refers to the concentration of compound (usually agonist) at which response is eighty percent of maximum.

Dialkylaminocarbonyl radicals, or secondary amine carbamoyl radicals, are those in which a dialkylamino substituent is joined to another atom by a carbonyl group, designated herein as CO. One example not intended to be limiting is diethylaminocarbonyl, in which $N(CH_2CH_2)_2$ is joined through a CO bond to an atom of another molecule, for example to the oxygen of phenol, to form a carbamate derivative. The product, $C_6H_5OCONH(CH_2CH_3)_2$, contains the $CON(CH_2CH_2)_2$ radical. A second non-limiting example is the 1-pyrrolidinecarbonyl radical, stylistically represented by A, when bonded to the oxygen of phenol, gives the carbamate product B, which contains the 1-pyrrolidinecarbonyl radical.

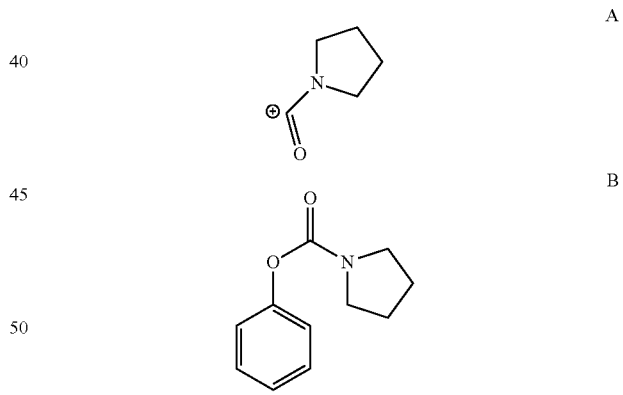

The secondary amine from which the dialkylaminocarbonyl radical is derived might be an N-alkyl amino acid. The terminology used herein to describe such radicals utilizes the well-known abbreviations for amino acids, coupled with widely used descriptors indicating N(α)-alkyl amino acids. The three letter codes for the naturally occurring amino acids (Eur. J. Biochem. 138:9-37 (1984)) are used herein. The secondary amine derived from naturally occurring amino acids, which gives rise to the said dialkylaminocarbonyl radicals, is described herein as an abbreviation encompassing the accepted three-letter amino acid abbreviations with the prefix N-Me. Thus, the secondary amine from which the dialkylaminocarbonyl radical is derived is referred to herein as N-Me-XXa-OH where Me denotes methyl and Xaa denotes generically any three-letter abbreviation for a naturally-occurring amino acid. The three-letter codes for the amino acids are widely known and can be found in Lehninger, *Biochemistry*, (Worth Publishers, New York, N.Y., 1978). The corresponding dialkylaminocarbonyl radical is referred to herein as CO—N-Me-Xaa-OH. As examples not intended to be limiting, the CO—N-Me-Ala-OH radical (wherein Xaa=Ala) has the stylized structure

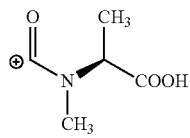

and the CO—N-Me-Leu-OH radical (wherein Xaa=Leu) has the stylized structure

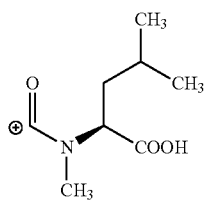

In likewise fashion, the secondary amine from which the dialkylaminocarbonyl radical is derived might be a di- or tri-peptide or di- or -tri-pseudopeptide, optionally with an N-alkylated N-terminus. For a dipeptide radical, the corresponding dialkylaminocarbonyl radical is referred to herein as CO—N-Me-Xaa-Xaa-OH. Thus, the CO—N-Me-Gly-Gly-OH radical can be represented as

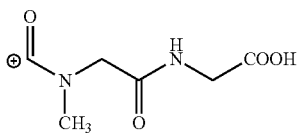

The stylized depictions of dialkylaminocarbonyl radicals herein are not meant to reflect actual chemical species, but are rather offered as a means to better understand the invention and the nomenclature used herein to describe the various embodiments. It will be understood that compounds of the invention containing amino acids refers to the natural (L) form, the (D) form, and the racemic (D,L) form.

In some embodiments, compounds of Formula I comprise

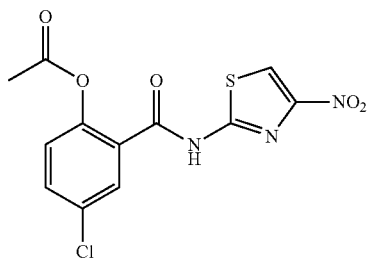

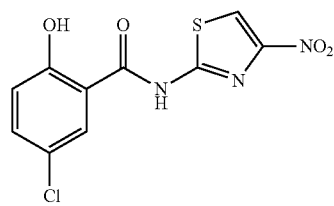

In some embodiments of the invention, compounds of Formula 1 comprise

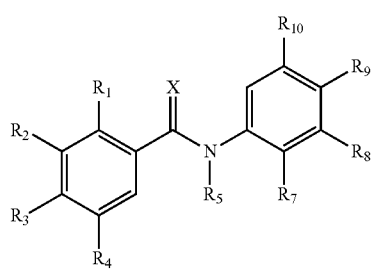

wherein
R1=OH;
R2 and R3=H;
R4 is selected from the set consisting of H, Cl, Br, F, CH3, OCH3, CF3, OCF3, and phenyl;
R5=H; and
R7, R8, R9, and R10 are each independently chosen from the group consisting of Cl, Br, F, CH3, CH2CH3, CH2Ph, CH=CH$_2$, C≡CH, C≡N, OCH$_3$, OCF$_3$, Ph, OPh, and NO$_2$.

In some embodiments of the invention, compounds of Formula 1 comprise

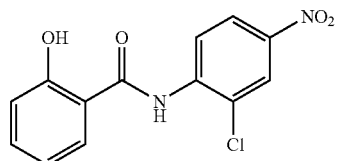

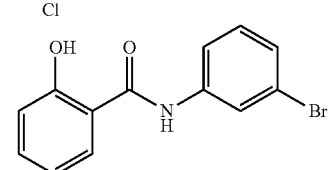

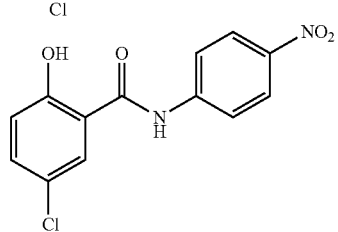

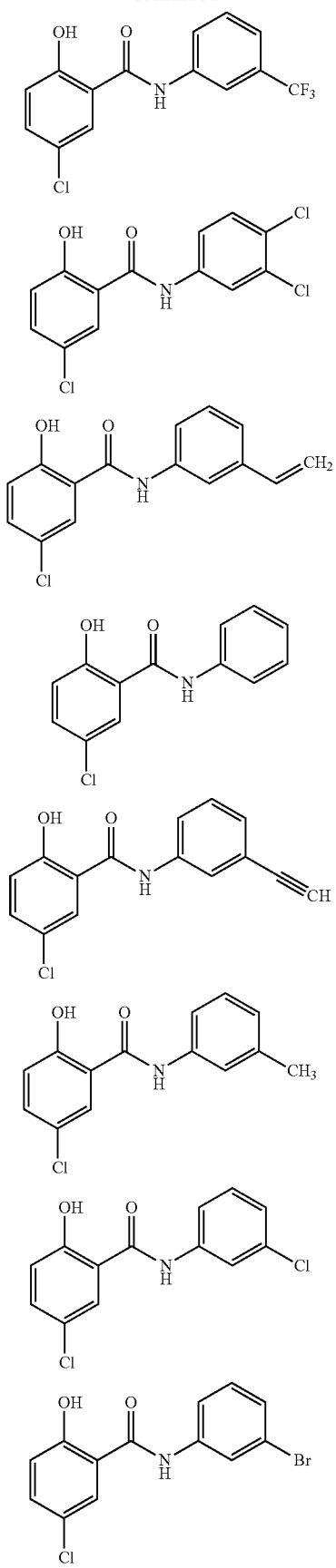
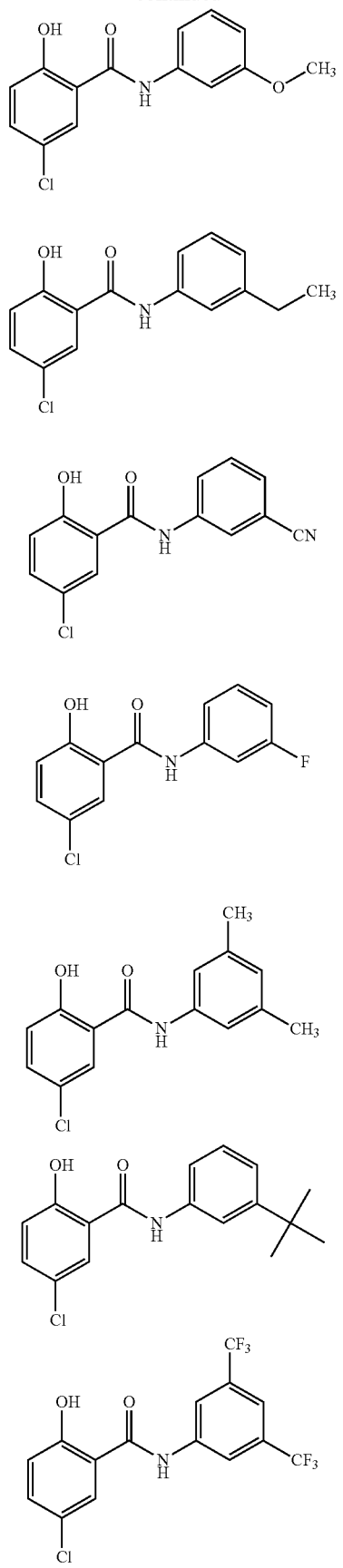

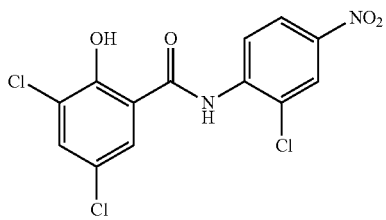

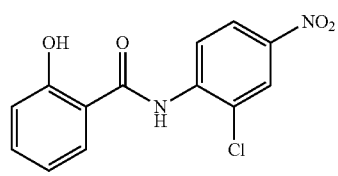

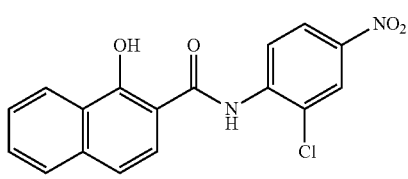

Compounds of Formula 1 which have little or no inherent binding affinity for either the orthosteric or allosteric sites of Group 1 mGluRs are contemplated and provided in the invention. Such compounds are derivatives of active elements of Formula 1 which are designed to degrade in a controlled fashion under conditions of use of compounds of the invention, ultimately providing an active agent of Formula 1. These derivatives of the active compounds of Formula 1, herein termed "prodrugs", are useful in that their chemical structure, although demonstrating little or no binding affinity, imparts properties of particular importance in the treatment of diseases or disorders mediated fully or partially by Group 1 mGluRs as disclosed herein. Such properties include, but are not limited to, enhancement of solubility in aqueous systems, improvement of pharmacokinetic parameters, improvement of purification procedures, enhancement of membrane permeability, and the provision of controlled release of the active principle. The degradation of the inert derivative to the active compound of Formula 1 may occur by simple chemical hydrolysis. Alternatively, said derivative may be a substrate for an enzyme which provides the active compound. Derivatives are chosen so that the chemical bond is cleavable under physiological conditions, whether chemical or enzymatic. In the case of the present invention, active compounds of Formula 1 possess a free phenolic —OH, and prodrug derivatives are esters or carbamates. It is well known in the art that certain inactive prodrug esters and carbamates of hydroxyl-containing drugs yield the drug after administration to a subject. For example, Dipivefrin, an inactive prodrug containing two tert-butyl esters, is cleaved to the drug adrenaline after administration to a subject, and valacyclovir, a valine ester, is cleaved to acyclovir after administration. For another example, the inactive prodrug bis(dimethylcarbamate) bambuterol is converted to the [beta]$_2$-sympathomimetic agent terbutaline used to achieve bronchodilation in the management of asthma. Terbutaline is formed from bambuterol by hydrolysis predominantly catalyzed by plasma cholinesterase (pChE, EC 3.1.1.8) (Nyberg, L. et al, *Br. J. Clin. Pharmacol.* 1998; 45(5); 471-8.

In some embodiments, prodrug compounds of Formula 1 comprise

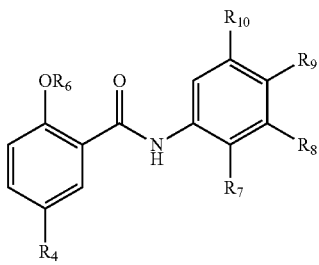

wherein
R4 is selected from the set consisting of H, Cl, Br, F, CH$_3$, OCH$_3$, CF$_3$, OCF$_3$, and phenyl;
R$_6$ is selected from the group consisting of COCH$_3$, COCH$_2$CH$_3$, COCH(CH$_3$)$_2$, COC(CH$_3$)$_3$, COPh, COCH$_2$Ph, COC$_6$H$_4$NO2(p), COC$_6$H$_4$OH(p), COC$_6$H$_4$NH$_2$(p), CON(CH$_3$)$_2$, CON(CH$_2$CH$_3$)$_2$, CON(CH$_3$)(CH$_2$CH$_3$), CON(CH$_2$Ph)$_2$, CON(CH$_3$)(CH$_2$Ph), 1-pyrrolidinecarbonyl, 2-carboxy-1-pyrrolidincarbonyl, (2S)-2-carboxy-1-pyrrolidinecarbonyl, (2R)-2-carboxy-1-pyrrolidinecarbonyl, 1-morpholinecarbonyl, 4-methyl-1-piperazinecarbonyl, sarcosine-N-carbonyl, CO-N-Me-Ala-OH, CO-N-Me-Val-OH, CO-N-Me-Leu-OH, CO-N-Me-Ile-OH, CO-N-Me-Val-OH, CO-N-Me-Met-OH, CO-N-Me-Phe-OH, CO-N-Me-Trp-OH, CO-Pro-OH, CO-N-Me-Gly-OH, CO-N-Me-Ser-OH, CO-N-Me-Thr-OH, CO-N-Me-Cys-OH, CO-N-Me-Tyr-OH, CO-N-Me-Asn-OH, CO-N-Me-Gln-OH, CO-N-Me-Asp-OH, CO-N-Me-Glu-OH, CO-N-Me-Lys-OH, CO-N-Me-Arg-OH, CO-N-Me-His-OH, CO-N-Me-Gly-Gly-OH, CO-N-Me-Gly-Gly-Gly-OH, CO-N-Me-Gly-Phe-OH, CO-N-Me-Gly-Glu-OH, CO-N-Me-Gly-Glu-Glu-OH, CO-N-Me-Glu-Glu-OH, CO-N-Me-Gly-Lys-OH, CO-N-Me-Gly-Lys-Lys-OH, CO-Pro-Glu-OH, CO-Pro-Glu-Glu-OH, CO-Pro-Gly-OH, CO-Pro-Lys-OH, CO-Pro-Lys-Lys-OH, CO-Pro-Gly-Lys-OH, and CO-Pro-Lys-Lys-OH; and
R7, R8, R9, and R10 are each independently chosen from the group consisting of Cl, Br, F, CH$_3$, CH$_2$CH$_3$, CH$_2$Ph, CH=CH$_2$, C≡CH, C≡N, OCH$_3$, OCF$_3$, Ph, OPh, and NO$_2$.

It will be appreciated that other amino acids not specifically identified herein might be utilized in prodrug compounds of Formula 1. These may be selected from the family of naturally occurring L-amino acids, that is, alanine, valine, leucine, isoleucine, proline, phenylalanine, tryptophan, methionine, glycine, serine, threonine, cysteine, cystine, tyrosine, asparagine, glutamine, aspartic acid, glutamic acid, lysine, arginine, and histidine. It will also be appreciated that, in addition to the L-amino acids herein described, unnatural D-amino acids may be employed in prodrug compounds of Formula 1. It will be further appreciated that, in addition to the specific prodrugs of Formula 1 disclosed herein, other peptide prodrugs are contemplated by the present invention. These include, but are not limited to, di-, tri-, tetra-, penta-, hexa-, hepta, octa-, nona-, and deca-peptides comprised of any of the natural L-amino acids or the unnatural D-amino acids or their N-methyl derivatives.

In some embodiments, prodrug compounds of Formula 1 comprise

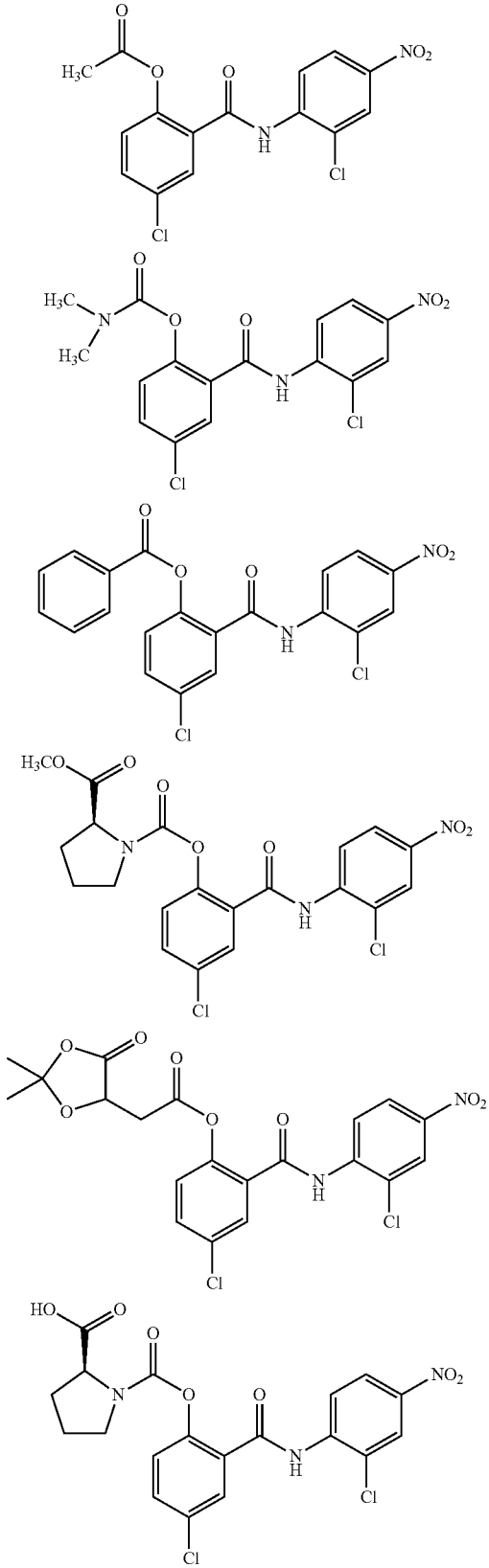

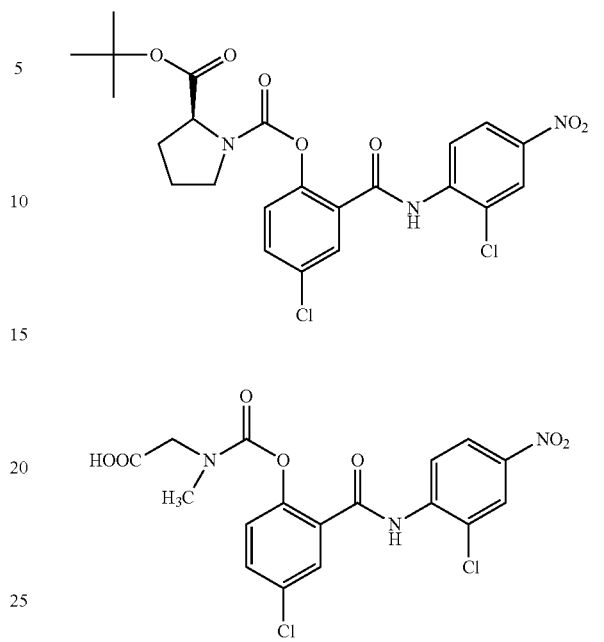

Prodrug derivative compounds of Formula 1 can be transformed into pharmaceutically acceptable salts by means well known to those with skill in the art. Such salts are intended to provide enhanced properties such as increased water solubility. Such salts are contemplated by the invention and provided herein. Such salts may be prepared by methods well-known to those with skill in the art. For example, an acidic prodrug derivative compound of Formula 1 may be dissolved in a solvent such as, inter alia, methanol, ethanol, or tetrahydrofuran and a molar equivalent amount of meglumine added to form the addition salt. Removal of the solvent or precipitation of the salt by addition of a cosolvent such as, inter alia, ether, petroleum ether, hexane, heptane, or toluene provides the purified salt. Alternatively, such salts may be prepared by methods disclosed in U.S. Pat. No. 5,028,625 to Motola et al. Alternatively, such salts may be prepared by methods disclosed in WO/2007/063335 to Klaveness.

In some embodiments of the invention, pharmaceutically acceptable salts of prodrug derivative compounds of Formula 1 comprise

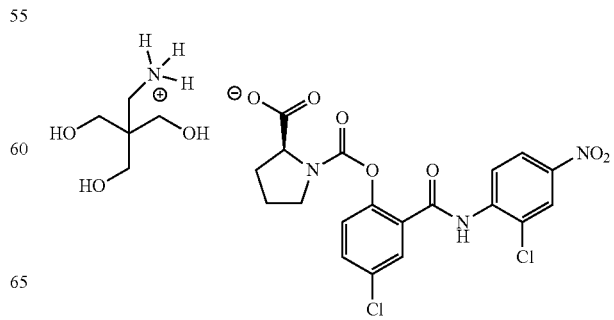

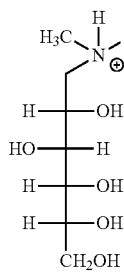
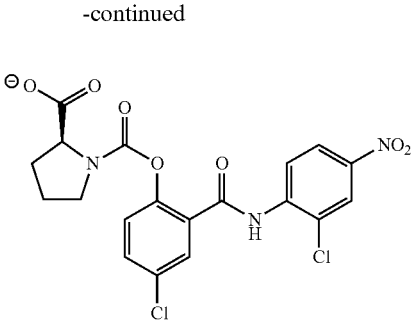

Compounds of Formula I are useful in modulating the functional action of Group I metabotropic glutamate receptors. Compounds of Formula I are useful in preventing and treating diseases or disorders caused by dysfunctional Group I metabotropic glutamate receptors. The ability of compounds of Formula I to act as allosteric modulators of these receptors can be assessed by measuring the degree of binding of a ligand to the orthosteric glutamate binding site in the presence of a compound of Formula I. Binding of a compound of Formula I to an allosteric site can induce a change in the conformation of the receptor, which in turn can influence the affinity of an orthosteric ligand for the primary (glutamate) receptor site. For example, the binding constant (K) of a ligand such as quisqualate (quisqualic acid, (2S)-2-amino-3-(3,5-dioxo-1,2,4-oxadiazolidin-2-yl)propanoic acid) can be altered if a compound of Formula I is bound to an allosteric binding site. The $K_i$ of the orthosteric ligand can be measured using radiolabelled ligand (for example $^3$H-quisqualate) by methods well known in the art. Assays of such altered orthosteric binding are commercially available (offered, for example, by Euroscreen SA, Gosselies, BE). The ability of compounds of Formula I to act as allosteric modulators of Group I metabotropic glutamate receptors can also be assessed by the ability of a compound to displace a known allosteric ligand, as two different ligands may compete for an allosteric binding site. For example, the ability of compounds of Formula I to function as allosteric ligands to mGluR1 may be assessed by their ability to displace the known mGluR1 allosteric ligand R214127. This may be measured by methods known in the art (Lavreysen, H. et al 2003; *Mol. Pharmacol.* 63:1082-1093). For an additional example, the ability of compounds of Formula I to function as allosteric ligands to mGluR5 may be assessed by their ability to displace the known mGluR5 allosteric ligand MPEP (2-methyl-6-(phenylethynyl)-pyridine). This may be measured by methods known in the art (Gasparini, F. et al 2002; *Bioorg. Med. Chem. Lett.* 12:407-409; Anderson, F. et al. 2002; *J. Pharmacol. Exp. Ther.* 303:1044-1051). Such measurement by displacement of MPEP by compounds of Formula I are commercially available (from, for example, Euroscreen SA, Gosselies, BE). The ability of compounds of Formula I to act as allosteric modulators of Group I metabotropic glutamate receptors can also be assessed by the ability of a compound to influence the function of the Group I metabotropic glutamate receptors. This may be measured by methods known in the art. For example, the measurement of the ability of a compound of Formula I to modulate Group I metabotropic glutamate receptors may be assessed by its ability to inhibit glutamate-induced phosphoinositide accumulation (Pin, J. et al 1995; *Neuropharm.* 34:1-26; Sortino, M. et al 1991; *Brain Res. Dev. Brain Res.* 61:169-172.). Another example of the ability of a compound of Formula I to modulate Group I metabotropic glutamate receptors may be assessed by its ability to inhibit glutamate-induced calcium release (Chen, Y et al 2007; *Mol. Pharmacol.* 71:1389-1398; Malherbe, P. et al 2003; *Mol. Pharmacol.* 64:823-832.)

The ability of compounds of Formula I to prevent or treat diseases or disorders of the central nervous system may be assessed by means well-known in the art. For example, a variety of preparations of central nervous system receptors have been described. The affinity of compounds of Formula I for such receptors, and the determination of agonism or antagonism displayed by compounds of Formula I relative to such receptors, is quantifiable. In addition, there are several animal models of human central nervous system disorders or diseases which may assay the activity of Compounds of Formula I (offered, for example, by NeuroDetective International, Wyncote, Pa.).

Compounds of Formula I are useful in a method of modulating Group I metabotropic glutamate receptor activity in a mammal in need of such modulation comprising the administration of an effective amount of the compound. The present invention is directed to the use of the compounds disclosed herein as modulators of metabotropic glutamate receptor activity. In addition to primates, especially humans, a variety of other mammals can be treated according to the method of the present invention.

In a like manner, the noncompetitive antagonist compounds of Formula I are useful in a method of inhibiting metabotropic glutamate receptor activity in a mammal in need of such inhibition comprising the administration of an effective amount of the compound. The present invention is directed to the use of the compounds of Formula I as noncompetitive antagonists of Group I metabotropic glutamate receptor activity. In addition to primates, especially humans, a variety of other mammals can be treated according to the method of the present invention.

Compounds of Formula 1 were found to bind with varying affinity and selectivity to mGluR1 and mGluR5. Briefly, stable recombinant cell lines expressing mGluR1 or mGluR5 and aequorin were treated with compounds of Formula 1 at various concentrations. The ability of test compound to ameliorate the efflux of calcium cations ($Ca^{++}$) in the presence of agonist (glutamate or quisqualate) is measured by detection of light emitted by the luminescent protein aequorin triggered by binding of $Ca^{++}$. Aequorin is a photoprotein isolated from luminescent jellyfish (like various *Aequorea* species e.g. *Aequorea victoria*). Aequorin is composed of two distinct units, the apoprotein apoaequorin, with an approximate molecular weight of 22 kDa, and the prosthetic group, coelenterazine, responsible for emission of light. In the presence of molecular oxygen the two components of aequorin assemble spontaneously, forming the functional protein. Four EF-hand type regions have been identified in the structure of Aequorin and at least 3 of them function as binding sites for Ca+2 ions: Ca+2 binding to these EF hands triggers a conformational change of the protein, that leads it to oxidize its prosthetic group, coelenterazine, into excited coelenteramide and CO2. As the excited coelenteramide relaxes to the ground state, blue light (wavelength=469 nm) is emitted and can be measured by a luminometer. Negative allosteric modulator activity of test compound is expressed as a percentage of the stimulation of reference agonist (glutamate) activity at its $EC_{80}$ concentration. Assay of Compounds was performed at Euroscreen SA, Gosselies, Belgium.

The in vitro binding of compounds of Formula 1 to mGluR1 and/or mGluR5, as determined by the aequorin assay, is a measure of the potential of these compounds to treat diseases and disorders partially or fully modulated by mGluR1 and/or mGluR5. It is understood that the magnitude of affinity of a compound for a Group 1 mGluR may not reflect its suitability as a therapeutic agent to treat diseases and disorders fully or partially mediated by Group 1 mGluRs. This is because metabotropic glutamate receptors mediate a wide variety of normal physiological processes, and agents which block the functionality of these receptors may produce pathological effects. Some disorders, for example, inter alia, central nervous system disorders, may be best treated with a negative allosteric modulator with moderate affinity for Group 1 mGluRs. Compounds of Formula 1 provided by the invention are intended to be effective therapeutic agents for treatment of diseases or disorders fully or partially mediated by Group 1 mGluRs. Compounds of Formula 1 with $EC_{50}$ in the range of 0.1 to 1000 nM are considered effective negative allosteric modulators. In some embodiments, compounds with $EC_{50}$ in the range of 1 to 1000 nM are considered effective negative allosteric modulators. In other embodiments, compounds with $EC_{50}$ in the range of 10 to 1000 nM are considered effective negative allosteric modulators. In still other embodiments, compounds with $EC_{50}$ in the range of 30 to 1000 nM are considered effective negative allosteric modulators. In yet other embodiments, compounds with $EC_{50}$ in the range of 100 to 1000 nM are considered effective negative allosteric modulators.

It was surprisingly discovered that some compounds of Formula 1 exhibited selective affinity for one of the Group1 mGluRs. It is understood that some diseases or disorders fully or partially mediated by Group 1 mGluRs may be best treated with compounds which selectively antagonize mGluR1 or mGluR5. It is also understood that some diseases or disorders fully or partially mediated by Group 1 mGluRs may be best treated with compounds which demonstrate little selectivity and which antagonize both mGluR1 and mGluR5. A measure of the selective affinity of the compounds of Formula 1 for these receptors can be made by striking a ratio of the $EC_{50}$ values. For any compound, the $EC_{50}$ for mGluR1 divided by the $EC_{50}$ for mGluR5 provides such a ratio. Thus, compounds with such a ratio less than 1.0 demonstrate selective affinity for mGluR1, and compounds with a ratio greater than 1.0 demonstrate selective affinity for mGluR5. In some embodiments, a compound of Formula 1 with a mGluR5/mGluR1 $EC_{50}$ ratio in the range of 0.01 to 0.8 is considered selective for mGluR1. In some embodiments, a compound of Formula 1 with a mGluR5/mGluR1 $EC_{50}$ ratio in the range of 1.25 to 100 is considered selective for mGluR5.

TABLE 1

Table 1 depicts the affinities and mGluR5/mGluR1 $EC_{50}$ ratio of representative compounds of Formula 1 having the structure

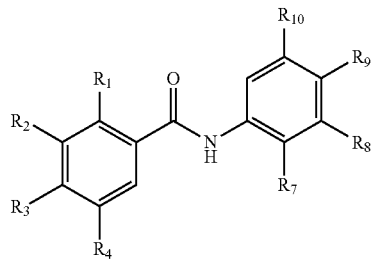

| Compound | R1 | R2 | R3 | R4 | R7 | R8 | R9 | R10 | mGluR1 $EC_{50}$ nM | mGluR5 $EC_{50}$ nM | mGluR1/mGluR5 Ratio |
|---|---|---|---|---|---|---|---|---|---|---|---|
| 1 | OH | H | H | Cl | Cl | H | NO$_2$ | H | 38 | 62 | 0.61 |
| 2 | OH | Cl | H | Cl | Cl | H | NO$_2$ | H | 1577 | 669 | 2.36 |
| 3 | OH | fused phenyl | | H | Cl | H | NO$_2$ | H | 603 | 262 | 2.30 |
| 4 | OH | H | H | H | Cl | H | NO$_2$ | H | 290 | 168 | 1.73 |
| 5 | OH | H | H | Cl | H | Cl | Cl | H | 179 | 90 | 1.99 |
| 6 | OH | H | H | Cl | H | H | H | H | 3041 | 731 | 4.16 |
| 7 | OH | H | H | Cl | H | H | NO$_2$ | H | 300 | 169 | 1.78 |
| 8 | OH | H | H | Cl | H | CH$_3$ | H | H | 2386 | 84 | 28.40 |
| 9 | OH | H | H | Cl | H | Br | H | H | 459 | 166 | 2.77 |
| 10 | OH | H | H | Cl | H | C≡CH | H | H | 932 | 122 | 7.64 |
| 11 | OH | H | H | Cl | H | CH=CH$_2$ | H | H | 371 | 48 | 7.73 |
| 12 | OH | H | H | Cl | H | CH$_2$CH$_3$ | H | H | 859 | 135 | 6.36 |
| 13 | OH | H | H | Cl | H | CF$_3$ | H | H | 273 | 127 | 2.15 |
| 14 | OH | H | H | Cl | H | Cl | H | H | 523 | 126 | 4.15 |
| 15 | OH | H | H | Cl | H | OCH$_3$ | H | H | 10000 | 260 | 38.46 |
| 16 | OH | H | H | Cl | H | CN | H | H | 10000 | 235 | 42.55 |
| 17 | OH | H | H | Cl | H | F | H | H | 598 | 138 | 4.33 |
| 18 | OH | H | H | Cl | H | C(CH$_3$)$_3$ | H | H | 334 | 238 | 1.40 |
| 19 | OH | H | H | Cl | H | CH$_3$ | H | CH$_3$ | 1145 | 122 | 9.39 |
| 20 | OH | H | H | Cl | H | CF$_3$ | H | CF$_3$ | 111 | 91 | 1.22 |
| 21 | CH$_3$CO(=O) | H | H | Cl | H | H | NO$_2$ | H | 94 | 91 | 1.03 |
| 22 | PhC(=O)O | H | H | Cl | H | H | NO$_2$ | H | 192 | 109 | 1.76 |
| 23 | (CH$_3$)$_2$NC(=O)O | H | H | Cl | H | H | NO2 | H | 10000 | 10000 | NA |

TABLE 1-continued

Table 1 depicts the affinities and mGluR5/mGluR1 EC$_{50}$ ratio of representative compounds of Formula 1 having the structure

| Compound | R1 | R2 | R3 | R4 | R7 | R8 | R9 | R10 | mGluR1 EC$_{50}$ nM | mGluR5 EC$_{50}$ nM | mGluR1/mGluR5 Ratio |
|---|---|---|---|---|---|---|---|---|---|---|---|
| 24 | (structure) | H | H | Cl | H | H | NO$_2$ | H | 95 | 59 | 1.61 |
| 25 | (structure) | H | H | Cl | H | H | NO$_2$ | H | 10000 | 10000 | NA |
| 26 | (structure) | H | H | Cl | H | H | NO$_2$ | H | 10000 | 10000 | NA |
| 27 | (structure) | H | H | Cl | H | H | NO$_2$ | H | 10000 | 10000 | NA |

NA = not applicable.
Values designated as 10000 indicate no activity was observed at 10,000 nM (10 μM).

It should be emphasized than the phenolic ester functionality (ArO(C=O)C) in compounds 21, 22, and 24 is sensitive to simple chemical hydrolysis. In addition, compounds containing this functionality may be substrates for esterase enzymes potentially present in the cell-based assay. Therefore, although these compounds may exhibit no inherent activity, hydrolysis or enzymatic cleavage under the conditions of the assay may provide Compound 1 which has potent binding activity, and the apparent activity of the ester compounds may be due to Compound 1 liberated from its ester derivatives in the course of the assay.

In addition to the salicylanilide derivatives depicted in Table 1, it was surprisingly found that certain thiazole derivatives of benzamide demonstrated in vitro activity. For example,

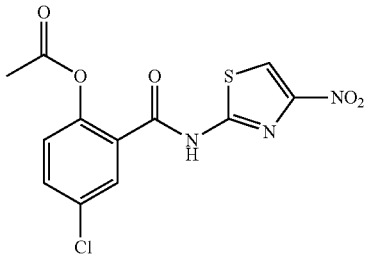 [SMILES: CC(=O)Oc1ccc(Cl)cc1C(=O)Nc1nc([N+](=O)[O-])cs1]

demonstrated binding of 6320 nM at mGluR1 and 2764 nM at mGluR5, and

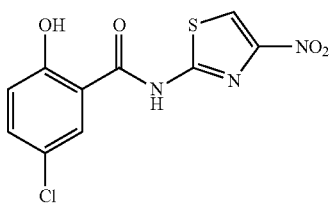 [SMILES: O=C(Nc1nc([N+](=O)[O-])cs1)c1cc(Cl)ccc1O]

demonstrated binding of 1759 nM at mGluR1 and 1254 nM at mGluR5.

As demonstrated herein, compounds of Formula I possess in vitro binding affinity for the Group 1 mGluRs and thus are useful in the treatment of diseases or disorders mediated by Group 1 mGluRs.

Certain compounds of Formula I were further evaluated for their ability to mediate neuropathic pain in a partial sciatic nerve ligation assay in the rat (Y. Shir and Z. Seltzer 1990; *Neurosci. Lett.*, 115:62-7). Briefly, under gas anesthesia, the skin and muscles of the thigh were reflected to expose the sciatic nerve. About one-third to one-half of the cross-sectional area of the nerve was tightly ligated using a 7-0 nylon suture. The incision was closed in layers (suture for muscle, surgical adhesive for skin). After a three-week recovery, the animals were dosed with either 10 or 49 μg Compound 1, 10 or 49 μg Compound 21, or 100 μg gabapentin by intrathecal injection. Treated rats were assayed at 1, 3, 5, and 24 hr using the paw withdrawal method (L. Randall and J. Selitto, 1957, *Arch. Int. Pharmacodynam.*, 111:409-19). As presented graphically in FIG. 1 and tabulated in Table 2, Compound 1 and Compound 21 were essentially as effective or more effective as gabapentin in reversing hyperalgesia. As illustrated in FIG. 1 and presented in Table 2, 49 μg of Compound 1 (0.15 μMol), is considerably more effective than 100 μg (0.58 μMol) gabapentin in this model of hyperalgesia. Indeed, 49 μg of Compound 21 (0.18 μMol) is nearly equipotent with 100 μg (0.58 μMol) gabapentin in the model. The Partial sciatic nerve ligation assay was performed at Eurofins/Product Safety Laboratories (Dayton, N.J.).

TABLE 2

Paw Withdrawal data.

| Rat | Group | Pre-injury | Pre-Dose | 1 hr | 3 hrs | 5 hrs | 24 hrs | Raw MPE (%) 1 hr | 3 hrs | 5 hrs | 24 hrs | % MPE (0-100) 1 hr | 3 hrs | 5 hrs | 24 hrs | AUC (0-5) |
|---|---|---|---|---|---|---|---|---|---|---|---|---|---|---|---|---|
| 1 | PSN Sx/ | 125 | 80 | 85 | 90 | 90 | 95 | | | | | | | | | |
| 7 | Vehicle | 165 | 130 | 150 | 125 | 115 | 130 | | | | | | | | | |
| 12 | | 160 | 130 | 115 | 120 | 130 | 120 | | | | | | | | | |
| 21 | | 165 | 65 | 70 | 65 | 75 | 75 | | | | | | | | | |
| 24 | | 200 | 90 | 100 | 105 | 95 | 75 | | | | | | | | | |
| 37 | | 130 | 95 | 105 | 100 | 95 | 75 | | | | | | | | | |
| 40 | | 155 | 85 | 70 | 100 | 80 | 85 | | | | | | | | | |
| Average | | 157.1 | 96.4 | 99.3 | 100.7 | 97.1 | 93.6 | | | | | | | | | |
| SD | | 25.0 | 24.8 | 28.2 | 19.9 | 19.3 | 22.9 | | | | | | | | | |
| SEM | | 9.4 | 9.4 | 10.7 | 7.5 | 7.3 | 8.6 | | | | | | | | | |
| N | | 7 | 7 | 7 | 7 | 7 | 7 | | | | | | | | | |
| 31 | Sham Sx/ | 125 | 160 | 220 | 175 | 160 | 165 | | | | | | | | | |
| 33 | Vehicle | 140 | 165 | 160 | 170 | 200 | 200 | | | | | | | | | |
| 36 | | 160 | 145 | 150 | 175 | 160 | 155 | | | | | | | | | |
| 39 | | 165 | 185 | 165 | 150 | 155 | 145 | | | | | | | | | |
| 41 | | 190 | 195 | 190 | 185 | 180 | 160 | | | | | | | | | |
| 45 | | 155 | 150 | 220 | 170 | 180 | 160 | | | | | | | | | |
| Average | | 155.8 | 166.7 | 184.2 | 170.8 | 172.5 | 164.2 | | | | | | | | | |
| SD | | 22.2 | 19.7 | 30.7 | 11.6 | 17.2 | 18.8 | | | | | | | | | |
| SEM | | 9.1 | 8.0 | 12.5 | 4.7 | 7.0 | 7.7 | | | | | | | | | |
| N | | 6 | 6 | 6 | 6 | 6 | 6 | | | | | | | | | |
| 2 | PSN Sx/ | 155 | 125 | 90 | 130 | 120 | 125 | −10.9 | 41.8 | 30.3 | 44.5 | 0.0 | 41.8 | 30.3 | 44.5 | 113.9 |
| 14 | SND | 150 | 85 | 90 | 120 | 120 | 105 | −10.9 | 27.5 | 30.3 | 16.2 | 0.0 | 27.5 | 30.3 | 16.2 | 85.3 |
| 20 | 121, 10 μg | 150 | 60 | 60 | 100 | 70 | 95 | −46.3 | −1.0 | −36.0 | 2.0 | 0.0 | 0.0 | 0.0 | 2.0 | 0.0 |
| 22 | | 160 | 105 | 105 | 100 | 130 | 100 | 6.7 | −1.0 | 43.6 | 9.1 | 6.7 | 0.0 | 43.6 | 9.1 | 53.7 |
| 23 | | 160 | 95 | 250 | 180 | 195 | 195 | 177.6 | 113.1 | 129.9 | 143.7 | 100.0 | 100.0 | 100.0 | 100.0 | 450.0 |
| 46 | | 130 | 70 | 160 | 150 | 100 | 85 | 71.5 | 70.3 | 3.8 | −12.1 | 71.5 | 70.3 | 3.8 | 0.0 | 251.7 |
| Average | | 150.8 | 90.9 | 125.8 | 130.0 | 122.5 | 117.5 | 31.3 | 41.8 | 33.6 | 33.9 | 29.7 | 39.9 | 34.7 | 28.6 | 159.1 |
| SD | | 11.1 | 23.7 | 69.2 | 31.0 | 41.4 | 40.2 | 81.5 | 44.2 | 55.0 | 57.0 | 44.4 | 39.7 | 36.2 | 38.5 | 165.6 |
| SEM | | 4.5 | 9.7 | 28.2 | 12.6 | 16.9 | 16.4 | 33.3 | 18.0 | 22.5 | 23.3 | 18.1 | 16.2 | 14.8 | 15.7 | 67.6 |
| N | | 6 | 6 | 6 | 6 | 6 | 6 | 6 | 6 | 6 | 6 | 6 | 6 | 6 | 6 | 6 |
| 9 | PSN Sx/ | 165 | 90 | 250 | 250 | 180 | 90 | 177.6 | 212.9 | 110.0 | −5.1 | 100.0 | 100.0 | 100.0 | 0.0 | 450.0 |
| 17 | SND 121, 49 μg | 190 | 55 | 250 | 150 | 130 | 55 | 177.6 | 70.3 | 43.6 | −54.6 | 100.0 | 70.3 | 43.6 | 0.0 | 334.2 |
| 18 | | 180 | 115 | 190 | 90 | 100 | 100 | 106.9 | −15.3 | 3.8 | 9.1 | 100.0 | 0.0 | 3.8 | 9.1 | 153.8 |
| 27 | | 140 | 80 | 140 | 130 | 80 | 80 | 48.0 | 41.8 | −22.7 | −19.2 | 48.0 | 41.8 | 0.0 | 0.0 | 155.5 |
| 35 | | 150 | 90 | 130 | 110 | 95 | 90 | 36.2 | 13.2 | −2.8 | −5.1 | 36.2 | 13.2 | 0.0 | 0.0 | 80.8 |
| 44 | | 160 | 95 | 235 | 250 | 130 | 90 | 159.9 | 212.9 | 43.6 | −5.1 | 100.0 | 100.0 | 43.6 | 0.0 | 393.6 |
| Average | | 164.2 | 87.5 | 199.2 | 163.3 | 119.2 | 84.2 | 117.7 | 89.3 | 29.2 | −13.3 | 80.7 | 54.2 | 31.8 | 1.5 | 261.3 |
| SD | | 18.6 | 19.7 | 54.4 | 70.0 | 35.8 | 15.6 | 64.1 | 99.9 | 47.6 | 22.1 | 30.1 | 43.0 | 39.3 | 3.7 | 150.8 |
| SEM | | 7.6 | 8.0 | 22.2 | 28.6 | 14.6 | 6.4 | 26.2 | 40.8 | 19.4 | 9.0 | 12.3 | 17.5 | 16.1 | 1.5 | 61.6 |
| N | | 6 | 6 | 6 | 6 | 6 | 6 | 6 | 6 | 6 | 6 | 6 | 6 | 6 | 6 | 6 |
| 8 | PSN Sx/ | 135 | 110 | 250 | 190 | 140 | 95 | 177.6 | 127.3 | 56.9 | 2.0 | 100.0 | 100.0 | 56.9 | 2.0 | 406.9 |
| 16 | SND 182, 10 μg | 125 | 80 | 130 | 140 | 110 | 105 | 36.2 | 56.0 | 17.1 | 16.2 | 36.2 | 56.0 | 17.1 | 16.2 | 183.4 |
| 26 | | 165 | 90 | 210 | 145 | 145 | 90 | 130.4 | 63.2 | 63.5 | −5.1 | 100.0 | 63.2 | 63.5 | 0.0 | 339.8 |
| 38 | | 175 | 95 | 200 | 100 | 70 | 55 | 118.7 | −1.0 | −36.0 | −54.6 | 100.0 | 0.0 | 0.0 | 0.0 | 150.0 |
| 42 | | 165 | 65 | 130 | 85 | 100 | 85 | 36.2 | −22.4 | 3.8 | −12.1 | 36.2 | 0.0 | 3.8 | 0.0 | 58.1 |

TABLE 2-continued

Paw Withdrawal data.

| | | Paw withdrawal thresholds (g; raw data) | | | | | Raw MPE (%) | | | | % MPE (0-100) | | | | AUC |
|---|---|---|---|---|---|---|---|---|---|---|---|---|---|---|---|
| Rat | Group | Pre-injury | Pre-Dose | 1 hr | 3 hrs | 5 hrs | 24 hrs | 1 hr | 3 hrs | 5 hrs | 24 hrs | 1 hr | 3 hrs | 5 hrs | 24 hrs | AUC (0-5) |
| 43 | | 160 | 85 | 120 | 130 | 70 | 75 | 24.4 | 41.8 | −36.0 | −26.3 | 24.4 | 41.8 | 0.0 | 0.0 | 120.1 |
| Average | | 154.2 | 87.5 | 173.3 | 131.7 | 105.8 | 84.2 | 87.2 | 44.1 | 11.5 | −13.3 | 66.1 | 43.5 | 23.5 | 3.0 | 209.7 |
| SD | | 19.6 | 15.1 | 53.9 | 37.0 | 32.6 | 17.4 | 63.5 | 52.7 | 43.3 | 24.7 | 37.4 | 38.8 | 29.2 | 6.5 | 135.0 |
| SEM | | 8.0 | 6.2 | 22.0 | 15.1 | 13.3 | 7.1 | 25.9 | 21.5 | 17.7 | 10.1 | 15.2 | 15.8 | 11.9 | 2.7 | 55.1 |
| N | | 6 | 6 | 6 | 6 | 6 | 6 | 6 | 6 | 6 | 6 | 6 | 6 | 6 | 6 | 6 |
| 10 | PSN Sx/ | 145 | 90 | 250 | 250 | 190 | 110 | 177.6 | 212.9 | 123.2 | 23.3 | 100.0 | 100.0 | 100.0 | 23.3 | 450.0 |
| 11 | SND 182, 49 μg | 125 | 95 | 160 | 125 | 140 | 160 | 71.5 | 34.6 | 56.9 | 94.1 | 71.5 | 34.6 | 56.9 | 94.1 | 233.4 |
| 13 | | 125 | 70 | 65 | 60 | 85 | 90 | −40.4 | −58.1 | −16.1 | −5.1 | 0.0 | 0.0 | 0.0 | 0.0 | 0.0 |
| 19 | | 160 | 120 | 250 | 105 | 120 | 80 | 177.6 | 6.1 | 30.3 | −19.2 | 100.0 | 6.1 | 30.3 | 0.0 | 192.6 |
| 29 | | 150 | 55 | 135 | 65 | 60 | 45 | 42.1 | −50.9 | −49.3 | −68.8 | 42.1 | 0.0 | 0.0 | 0.0 | 63.1 |
| 50 | | 130 | 95 | 100 | 130 | 85 | 100 | 0.8 | 41.8 | −16.1 | 9.1 | 0.8 | 41.8 | 0.0 | 9.1 | 84.8 |
| Average | | 139.2 | 87.5 | 160.0 | 122.5 | 113.3 | 97.5 | 71.5 | 31.1 | 21.5 | 5.6 | 52.4 | 30.4 | 31.2 | 21.1 | 170.6 |
| SD | | 14.6 | 22.5 | 76.7 | 69.0 | 47.1 | 37.9 | 90.4 | 98.5 | 62.5 | 53.7 | 45.6 | 38.5 | 40.8 | 36.9 | 161.6 |
| SEM | | 6.0 | 9.2 | 31.3 | 28.2 | 19.2 | 15.5 | 36.9 | 40.2 | 25.5 | 21.9 | 18.6 | 15.7 | 16.6 | 45.1 | 66.0 |
| N | | 6 | 6 | 6 | 6 | 6 | 6 | 6 | 6 | 6 | 6 | 6 | 6 | 6 | 6 | 6 |
| 3 | PSN Sx/ | 120 | 110 | 145 | 70 | 60 | 85 | 53.9 | −43.8 | −49.3 | −12.1 | 53.9 | 0.0 | 0.0 | 0.0 | 80.8 |
| 4 | Gabapentin, | 160 | 65 | 250 | 125 | 130 | 110 | 177.6 | 34.6 | 43.6 | 23.3 | 100.0 | 34.6 | 43.6 | 23.3 | 262.9 |
| 15 | 100 μg | 140 | 90 | 190 | 125 | 85 | 80 | 106.9 | 34.6 | −16.1 | −19.2 | 100.0 | 34.6 | 0.0 | 0.0 | 219.3 |
| 28 | | 145 | 75 | 100 | 90 | 100 | 75 | 0.8 | −15.3 | 3.8 | −26.3 | 0.8 | 0.0 | 3.8 | 0.0 | 5.1 |
| 32 | | 130 | 85 | 120 | 165 | 140 | 135 | 24.4 | 91.7 | 56.9 | 58.7 | 24.4 | 91.7 | 56.9 | 58.7 | 276.8 |
| 47 | | 185 | 125 | 185 | 230 | 65 | 105 | 101.0 | 184.4 | −42.7 | 16.2 | 100.0 | 100.0 | 0.0 | 16.2 | 350.0 |
| Average | | 146.7 | 91.7 | 165.0 | 134.2 | 96.7 | 98.3 | 77.4 | 47.7 | −0.6 | 6.7 | 63.2 | 43.5 | 17.4 | 16.4 | 199.1 |
| SD | | 23.2 | 22.3 | 54.6 | 57.2 | 33.1 | 22.7 | 64.3 | 81.6 | 43.9 | 32.2 | 43.7 | 43.5 | 25.8 | 23.0 | 130.3 |
| SEM | | 9.5 | 9.1 | 22.3 | 23.4 | 13.5 | 9.3 | 26.3 | 33.3 | 17.9 | 13.1 | 17.8 | 17.8 | 10.5 | 9.4 | 53.2 |
| N | | 6 | 6 | 6 | 6 | 6 | 6 | 6 | 6 | 6 | 6 | 6 | 6 | 6 | 6 | 6 |

PSN/SND-121 is Compound1;
PSN/SND-182 is Compound 21;
PSN/Vehicle is 9% DMSO/27%
Cremophor/64% Saline,
Sx is surgery,
SD is Standard Deviation,
SEM is Standard Error of the Mean,
N is Number of Animals,
MPE is Maximum Percent Effect As demonstrated herein, compounds of Formula I possess in vivo binding activity as a result of their affinity to bind at Group 1 mGluRs as evidenced by their ability to mediate hyperalgesia and thus are useful in the treatment of diseases or disorders mediated by Group 1 mGluRs.

The subject treated in the present method is a mammal in which modulation, inhibition, or attenuation of Group I metabotropic glutamate receptor activity is desired. The term "therapeutically effective amount" or "effective amount" means the amount of the compound of Formula I that will provide such modulation, inhibition, or attenuation.

As used herein, the terms "treatment" and "treating" refer to any process wherein there may be a slowing, interrupting, arresting, controlling, ameliorating, lessening, regulating, or stopping of the progression of the disorders mediated by Group 1 mGluRs including, but not limited to those described herein, but does not necessarily indicate a total elimination of all symptoms of the disorders. "Treatment" and "treating" may also refer to prophylactic therapy of the disorders mediated by Group 1 mGluRs including, but not limited to those described herein.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing one or more compounds of Formula I and a pharmaceutically acceptable carrier. By "pharmaceutically acceptable" it is meant the carrier, diluent or excipient must be devoid of intrinsic biological activity, and be compatible with the other ingredients of the formulation and not deleterious to the recipient thereof.

The terms "administration of" and or "administering" a compound should be understood to mean providing a compound of Formula I or a prodrug of a compound of Formula I or a composition containing a compound or prodrug of a compound of Formula 1 to an individual in need of treatment by a route generally accepted by those with skill in the art. Routes of such administration include, but are not limited to, oral, buccal, sublingual, inhalation, topical, transcutaneous, intravenous, subcutaneous, intraperitoneal, transdermal, intracerebroventricular, intrathecal, intracerebral implant, and depot implant.

Group I metabotropic glutamate receptors have been implicated in a wide range of biological functions. This has suggested a potential role for these receptors in a variety of disease processes in humans or other species.

Compounds of Formula I have utility in treating a variety of neurological and psychiatric disorders associated with glutamate dysfunction, including one or more of the following conditions or diseases: cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias including tremor (such as rest tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalized myoclonus and focal myoclonus), tics (including simple tics, complex tics and symptomatic tics), and dystonia (including generalized dystonia such as iodiopathic dystonia, drug-induced dystonia, symptomatic dystonia and paroxysmal dystonia, and focal dystonia such as blepharospasm, oromandibular dystonia, spasmodic dysphonia, spasmodic torticollis, axial dystonia, dystonic writer's cramp and hemiplegic dystonia)]; obesity, bulimia nervosa and compulsive eating disorders; pain including bone and joint pain (osteoarthritis), repetitive motion pain, dental pain, cancer pain, myofacial pain (muscular injury, fibromyalgia), perioperative pain (general surgery, gynecological), chronic pain, neuropathic pain, post-traumatic pain, trigeminal neuralgia, migraine and migraine headache; obesity or eating disorders associated with excessive food intake and complications associated therewith; attention-deficit/hyperactivity disorder; conduct disorder; mood disorders including depressive disorders, bipolar disorders, mood disorders due to a general medical condition, and substance-induced mood disorders; muscular spasms and disorders associated with muscular spasticity or weakness including tremors; urinary incontinence; amyotrophic lateral sclerosis; neuronal damage including ocular damage, retinopathy or macular degeneration of the eye, hearing loss or tinnitus; emesis, brain edema and sleep disorders including narcolepsy. Illustrative examples of the neuropathic pain include diabetic polyneuropathy, entrapment neuropathy, phantom pain, thalamic pain after stroke, post-herpetic neuralgia, atypical facial neuralgia pain after tooth extraction and the like, spinal cord injury, trigeminal neuralgia and cancer pain resistant to narcotic analgesics such as morphine. The neuropathic pain includes the pain caused by either central or peripheral nerve damage. And it includes the pain caused by either mononeuropathy or polyneuropathy. Compounds of Formula 1 are intended to be used for the prevention and/or delay of progression of pain.

In accordance with the present invention, the compounds of Formula I are useful in the treatment of disorders of the gastro-intestinal and urinary tract. In particular compounds of Formula I are useful in the treatment of conditions associated with visceral hypersensitivity, discomfort/pain and/or altered motor dysfunctions.

Disorders of the GI tract are well known to the expert. These disorders include Gastro-Esophageal Reflux Disease (GERD), Functional Gastro-intestinal Disorders and Postoperative Ileus. Functional Gastro-intestinal Disorders (FGIDs) are defined as chronic or recurrent conditions associated with abdominal symptoms without organic cause using conventional diagnostic measures. A cardinal symptom present in many FGIDs is visceral pain and/or discomfort. FGIDs include Functional Dyspepsia (FD), functional heartburn (a subset of GERD), Irritable Bowel Syndrome (IBS), Functional Bloating, Functional Diarrhea, Chronic Constipation, Functional Disturbances of the Biliary Tract as well as other conditions (see *Gut* 1999; Vol. 45 Suppl. II).

Post-operative Ileus is defined as failure of aboral passage of intestinal contents due to transient impairment of GI motility following abdominal surgery.

Disorders of the Urinary Tract comprise conditions associated with functional disturbances and/or discomfort/pain of the urinary tract. Examples of disorders of the urinary tract include but are not limited to incontinence, benign prostatic hyperplasia, prostatitis, detrusor hyperreflexia, outlet obstruction, urinary frequency, nocturia, urinary urgency, overactive bladder (OAB), pelvic hypersensitivity, urge incontinence, urethritis, prostatodynia, cystitis, idiopathic bladder hypersensitivity and the like. OAB is a syndrome characterized by urgency, with or without urinary incontinence, and usually with increased voiding frequency and nocturia.

Gastro-Esophageal Reflux Disease (GERD) results from the retrograde flow of gastric contents into the esophagus. It is the most common ailment in the upper gastro-intestinal tract; its cardinal feature and symptom is commonly known as "heartburn". A major factor considered for GERD is an incompetence of the Lower Esophageal Sphincter that opens transiently and allows passage of material (e.g. meal, acidic fluid or bile), from the stomach into the esophagus. This motor event denominated Transient Lower Esophageal Sphincter Relaxation (TLESR) occurs more often in patients suffering from GERD than in healthy subjects and occurs more often in infants with regurgitation. Current standard therapies in GERD aim at suppressing gastric acid secretion or enhancing gastrointestinal motility to limit the exposure of the esophagus to acidic gastric contents. Frequent exposure of the esophageal mucosa to acid can trigger pain (often perceived as heartburn) and lead to erosions. It can also lead to extra-esophageal disorders such as asthma, cough and laryngitis. To date, there is no treatment available which reduces the occurrence of TLESRs and, thereby, the symptoms associated with GERD or regurgitation in infants.

Functional Dyspepsia (FD) is defined as a condition associated with a heterogeneous pattern of upper abdominal symptoms including discomfort, pain, aching, bloating, belching, fullness, early satiety, nausea and vomiting, burning and indigestion Almost 80% of patients with Functional Dyspepsia have two or more of the above mentioned symptoms of the upper GI tract. The pathophysiological abnormalities observed in FD are as follows: Impaired gastric accommodation upon meal intake, hypersensitivity to gastric distension, delayed gastric emptying, autonomous and/or central nervous system disorder, exaggerated phasic contractile activity, abnormalities of the gastric electrical rhythm, duodenal hypersensitivity to lipids or acid, small intestinal dysmotility. Meals evoke symptoms in more than 75% of FD patients, and symptoms increase with meal ingestion in more than 90% of patients. Therefore, a treatment that prepares the stomach to meal intake has the potential to reduce meal-evoked symptoms. In fact, low fasting volume (not postprandial volume) was found to be an independent predictor for reduced meal size and post-meal symptoms in FD patients (Delgado-Aros et al., *Gastroenterology*, 2004; 127:1685-1694).

Irritable Bowel Syndrome (IBS) is a chronic or remittent gastrointestinal illness characterized by symptoms that include abdominal pain and/or discomfort, bloating and bowel disturbances, which may be either diarrhea or constipation or a bowel habit that has features of both.

Pain and/or Discomfort is often associated with FGIDs, disorders of the urinary tract and post-operative ileus; it is not only a symptom of GERD. Patients suffering from Irritable Bowel Syndrome (IBS), dyspepsia, diseases of the biliary tract, pancreas, urinary bladder and post-operative conditions report pain and discomfort. Visceral hypersensitivity has been discovered as a key phenomenon in many patients suffering from conditions like IBS, dyspepsia, GERD, functional heartburn and other conditions listed above. To date, there is no medication available which specifically treats visceral hypersensitivity and, thereby, reduces symptoms of pain/discomfort in patients suffering from GERD, functional heartburn, IBS, dyspepsia, diseases of the biliary tract, pancreas, urinary bladder and post-operative conditions. Pain, as used in this specification, includes visceral pain and/or visceral discomfort.

A further aspect of the invention relates to the use of compounds of Formula I for the treatment of FGIDs (e.g., functional heartburn, FD, IBS).

A further aspect of the invention relates to the use of compounds of Formula I for the treatment of disorders of the urinary tract.

A further aspect of the invention relates to the use of compounds of Formula I for the treatment of post-operative ileus.

A further aspect of the invention relates to the use of compounds of Formula I for the treatment of pain associated with disorders of the gastrointestinal and urinary tract.

A further aspect of the invention relates to the use of compounds of Formula I for the treatment of altered motor function associated with disorders of the gastro-intestinal and urinary tract.

A further aspect of the invention relates to the use of compounds of Formula I for the treatment of pain associated with post-operative ileus.

Compounds of Formula I have utility in the prevention and treatment of disorders of the skin wholly or partially mediated by Group I metabotropic glutamate receptors.

A further aspect of the invention relates to the use of compounds of Formula I for the prevention and treatment of disorders of the skin wholly or partially mediated by Group I metabotropic glutamate receptors.

The compounds of Formula I may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with one or more compound of Formula I. When one or more compound of Formula I is used contemporaneously with one or more other drugs, a pharmaceutical composition in unit dosage form containing such other drugs and the compound(s) of Formula I is preferred. However, the combination therapy may also include therapies in which the compound(s) of Formula I and one or more other drugs are administered on different overlapping schedules. It is also contemplated that when used in combination with one or more other active ingredients, the compounds of Formula I and the other active ingredients may be used in lower doses than when each is used singly. Accordingly, the pharmaceutical compositions of the present invention include those that contain one or more other active ingredients, in addition to one or more compound of Formula I.

The above combinations include combinations of one or more compound of Formula I not only with one other active compound, but also with two or more other active compounds. Likewise, compounds of Formula I may be used in combination with other drugs that are used in the prevention, treatment, control, amelioration, or reduction of risk of the diseases or conditions for which compounds of Formula I are useful. Such other drugs may be administered, by a route and in an amount commonly used therefor, contemporaneously or sequentially with one or more compound of Formula I. When one or more compound of Formula I is used contemporaneously with one or more other drugs, a pharmaceutical composition containing such other drugs in addition to the compound(s) of Formula I is preferred. Accordingly, the pharmaceutical compositions of Formula I include those that also contain one or more other active ingredients, in addition to one or more compound of Formula I.

Drugs suitable for combination with compounds of Formula 1 are well known to those with skill in the art, and can be identified by inspection of, inter alia, in Physician's Desk Reference (Medical Economics Company, Montvale, N.J.) and The Merck Index (Merck and Co., Inc., Whitehouse Station, N.J.).

In one embodiment, the subject compound may be employed in combination with anti-Alzheimer's agents, beta-secretase inhibitors, gamma-secretase inhibitors, HMG-CoA reductase inhibitors, NSAID's including ibuprofen, vitamin E, and anti-amyloid antibodies.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amitriptyline, amobarbital, amoxapine, bentazepam, benzoctamine, brotizolam, bupropion, busprione, butabarbital, butalbital, capuride, carbocloral, chloral betaine, chloral hydrate, chlordiazepoxide, clomipramine, clonazepam, cloperidone, clorazepate, clorethate, clozapine, cyprazepam, desipramine, dexclamol, diazepam, dichloralphenazone, divalproex, diphenhydramine, doxepin, estazolam, ethchlorvynol, etomidate, fenobam, flunitrazepam, flurazepam, fluvoxamine, fluoxetine, fosazepam, glutethimide, halazepam, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, reclazepam, roletamide, secobarbital, sertraline, suproclone, temazepam, thioridazine, tracazolate, tranylcypromaine, trazodone, triazolam, trepipam, tricetamide, triclofos, trifluoperazine, trimetozine, trimipramine, uldazepam, venlafaxine, zaleplon, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl(benzhexyl)hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with acetophenazine, alentemol, benzhexyl, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, risperidone, sulpiride, tetrabenazine, trihexyphenidyl, thioridazine, thiothixene or trifluoperazine.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form.

In another embodiment, the subject compound may be employed in combination with an anoretic agent such as aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; selective serotonin reuptake inhibitor (SSRI); halogenated amphetamine derivatives, including chlorphentermine, cloforex, clortermine, dexfenfluramine, fenfluramine, picilorex and sibutramine; and pharmaceutically acceptable salts thereof.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, .alpha.-adrenoreceptor antagonists, neurokinin-1 receptor antagonists, atypical anti-depressants, benzodiazepines, agonists or antagonists, especially $5\text{-HT}_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In another embodiment, the subject compound may be employed in combination with an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the subject compound may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antitussive such as codeine, hydrocodone, caramiphen, carbetapentane, or dextramethorphan; a diuretic; and a sedating or non-sedating antihistamine.

In still another embodiment, compounds of Formula I may be employed in combination with anticancer agents including, but not limited to mitomycin C, cyclophosphamide, busulfan, ifosfamide, isosfamide, 5'-deoxy-5-fluoro-N-pentyloxycarbonyl-cytidine, tamoxifen, melphalan, hexamethylmelamine, thiotepa, chlorambucil, methyl-CCNU, temozolomide, dibromodulcitol, methotrexate, trimextrate, aldesleukin, interferon-alpha-2b, interleukin-2, dacarbazine, gemcitabine, capecitabine, azacytidine, 5-fluorouracil, cytarabine, 2-fluorodeoxy cytidine, piritrexim, methotrexate, idatrexate, tomudex, trimetrexate, doxorubicin, epirubicin, etoposide, teniposide, mitoxantrone, irinotecan, 7-ethyl-10- hydroxy-camptothecin, topotecan, paclitaxel, docetaxel, vinblastine, vincristine, vinorelbine, cisplatin, oxaliplatin, spiroplatinum, and carboplatinum.

The compounds of Formula I may be administered by oral, parenteral (e.g., intramuscular, intraperitoneal, intravenous, ICV, intracisternal injection or infusion, subcutaneous injection, depot, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of Formula I may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874, to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of Formula I may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, flavoring and coloring agents.

The pharmaceutical compositions may be in the form of sterile injectable aqueous solutions, micellar formulations or oleaginous suspensions. Suspensions may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables. The pharmaceutical compositions for use as sterile injectable solutions may be colloidal compositions consisting of polymeric micelles which contain within compounds of Formula I (U.S. Pat. No. 6,338,859 to Leroux, J. et al 2000).

The compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of Formula I are employed. It is intended that topical application according to the present invention shall include mouth washes, dentifrices, and gargles.

In the treatment of conditions which require negative allosteric modulation of Group 1 metabotropic glutamate receptor activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets, capsules, caplets, or pills containing 1.0 to 1000 milligrams of the active ingredient, particularly 1.0, 5.0, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day. This dosage regimen may be adjusted by healthcare providers with knowledge and skill in the art to provide the optimal therapeutic response. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Compounds of Formula 1 may be prepared by methods known to those of skill in the art, or may be commercially available. Compound 1 (Table 1) is available from Sigma-Aldrich (St. Louis, Mo., Cat. No. N3510). Compound 6 (Cat. No. 250581) is also available from Aldrich. Compound 5 is available from TCI America (Portland, Oreg., Cat. No. 10668). The benzamides may be synthesized by condensing the appropriate benzoic acid derivative with a chosen amine. Typically, a benzoic acid or benzoyl chloride derivative is reacted with the appropriate amine in a solvent for a specified time at a specified temperature, and the product amine is isolated and optionally purified. Some compounds of Formula 1 have been disclosed, although the inventors could find no reference to prior use of compounds of Formula 1 used to treat disorders and diseases moderated by Group 1 mGluRs. For example, compound 1 (Table 1) is a well-known pharmaceutical substance, and compound 5 is a well-known bactericide. Compound 3 is disclosed in WO 2004041256; compound 10 is disclosed in WO 2005007151; compounds 6, 13, 14, 17, 19, and 20 are disclosed in US Pre-grant Publication 2005018700; and compound 21 is described in Schraufstatter, E. et al 1961; Zeitschr. fuer Naturfor. 16b:95-108.

EXAMPLES

For the purposes of clarification of the 1H NMR spectral data, the designations in Formula II are followed.

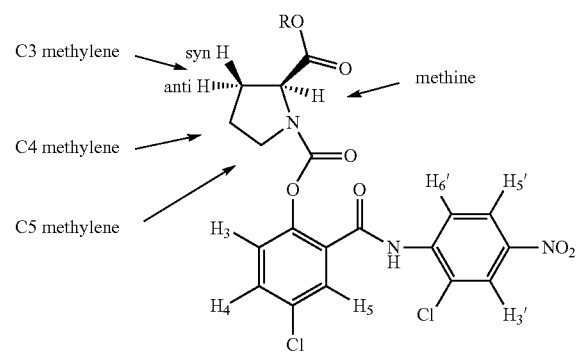

Formula II

Example 1

N-(2-chloro-4-nitrophenyl)-2 hydroxybenzamide (Compound 4)

The method disclosed in U.S. Pat. No. 3,079,297 to Shraufstatter et al with minor variations was utilized. A boiling solution of salicylic acid (1.03 g, 7.46 mmol) and 2-chloro-4-nitroaniline (1.29 g, 7.46 mmol) in xylenes (20 mL) was treated dropwise with a solution of phosphorous trichloride in dichloromethane 2.0M, 1.50 mL, 0.40 equiv.), and the resulting solution was refluxed (137° C.) for four hours. The solution was cooled to about 125° C. An oily residue covered the bottom and sides of the reaction vessel. The hot reaction solution was transferred by glass pipette to a beaker and was allowed to cool to room temperature while being stirred rapidly. The product separated, was collected by filtration, and washed with hexanes, then recrystallized from ethanol. The title compound was obtained, MP 218-220° C. (dec.). $^1$HNMR (500 MHz, DMSO-$d_6$): δ 7.02 (m, 1H, H3), 7.07 (m, 1H, H5), 7.49 (m, 1H, H4), 8.04 (m, 1H, H6), 8.28 (m, 1H, H5'), 8.41 (m, 1H, H3'), 8.85 (m, 1H, H6'), 11.8 (s, 1H, NH), 12.34 (s, 1H, OH).

Example 2

3,5-dichoro-N-(2-chloro-4-nitrophenyl)-2 hydroxy-benzamide (Compound 2)

This material was prepared according to the method of Example 1 using 3,5-dichlorosalicylic acid and 2-chloro-4-nitroaniline, with reagents and solvents employed in similar molar ratios. $^1$HNMR (500 MHz, DMSO-$d_6$): δ 7.85 (m, 1H, H4), 7.98 (m, 1H, H5), 8.29 (m, 1H, H5'), 8.04 (m, 1H, H6), 8.44 (m, 1H, H3'), 8.55 (m, 1H, H6').

Example 3

2-Hydroxy-4-chloro-N-4-nitrophenylbenzamide (Compound 7)

This material was prepared according to the method of Example 1 using 5-chlorosalicylic acid and 4-nitroaniline, with reagents and solvents employed in similar molar ratios. $^1$HNMR (500 MHz, DMSO-d$_6$): δ 7.04 (m, 1H, H3), 7.48 (m, 1H, H4), 7.84 (m, 1H, H6), 7.99 (m, 2H, H2' and H6'), 8.27 (m, 2H, H3' and H5').

Example 4

5-Chloro-2-hydroxy-N-(3-vinylphenyl)benzamide (Compound 11)

This material was prepared according to the method of Example 1 using 5-chlorosalicylic acid and 3-vinylaniline, with reagents and solvents employed in similar molar ratios. $^1$HNMR (500 MHz, DMSO-d$_6$): δ 5.32 (m, 1H, C═CH$_2$ cis), 5.83 (m, 1H, C═CH$_2$trans), 6.75 (m, 1H, ArCH═CH$_2$), 7.02 (m, 1H, H3), 7.28 (m, 1H, H6'), 7.37 (m, 1H, H5'), 7.49 (m, 1H, H4), 7.62 (m, 1H, H4'), 7.80 (m, 1H, H2'), 7.90 (m, 1H, H6).

Example 5

5-Chloro-2-hydroxy-N-(3-ethylphenyl)benzamide (Compound 12)

This material was prepared according to the method of Example 1 using 5-chlorosalicylic acid and 3-ethylaniline, with reagents and solvents employed in similar molar ratios. $^1$HNMR (500 MHz, DMSO-d$_6$): δ 1.20 (t, 3H), 2.62 (q, 1H), 7.02 (m, 2H), 7.28 (m, 1H), 7.47 (m, 1H), 7.54 (m, 1H), 7.56 (br s, 1H), 7.90 (m, 1H), 10.34 (s, 1H).

Example 6

5-Chloro-2-hydroxy-N-(3-methoxyphenyl)benzamide (Compound 15)

This material was prepared according to the method of Example 1 using 5-chlorosalicylic acid and m-anisidine, with reagents and solvents employed in similar molar ratios. $^1$HNMR (500 MHz, DMSO-d$_6$): δ 3.72 (s, 3H), 6.74 (m, 1H), 7.09 (m, 1H), 7.26 (br m, 2H), 7.40 (br s, 1H), 7.47 (m, 1H), 7.88 (m, 1H), 10.34 (s, 1H).

Example 7

5-Chloro-N-(3-cyanophenyl)-2-hydroxybenzamide (Compound 16)

This material was prepared according to the method of Example 1 using 5-chlorosalicylic acid and 3-aminobenzonitrile, with reagents and solvents employed in similar molar ratios. $^1$HNMR (500 MHz, DMSO-d$_6$): δ 3.72 (s, 3H), 6.74 (m, 1H), 7.05 (m, 1H), 7.45 (m, 1H), 7.58 (br m, 2H), 7.83 (m, 1H), 7.88 (m, 1H), 8.19 (br s, 1H), 10.59 (s, 1H).

Example 8

5-Chloro-N-(3-tert-butylphenyl)-2-hydroxybenzamide (Compound 18)

This material was prepared according to the method of Example 1 using 5-chlorosalicylic acid and 3-tert-butylaniline with reagents and solvents employed in similar molar ratios. $^1$HNMR (500 MHz, DMSO-d$_6$): δ 1.28 (s, 9H), 7.00 (d, 1H), 7.18 (m, 1H), 7.24 (m, 1H), 7.46 (dd, 1H), 7.56 (m, 1H), 7.68 (m, 1H), 7.95 (d, 1H), 10.38 (s, 1H), 11.90 (br s, 1H).

Example 9

4-Chloro-2-(2-chloro-4-nitrophenylcarbamoyl)phenyl benzoate (Compound 22)

A suspension of 5-Chloro-N-(2-chloro-4-nitrophenyl)-2-hydroxybenzamide (1.27 g., 3.88 mmol) in pyridine (15 mL) was treated with 4-dimethylaminopyridine (30 mg) and benzoyl chloride (0.49 mL, 4.27 mmol) was introduced dropwise. The suspension was warmed to 50° C. for one hour then cooled to room temperature and stirred for 17 hours. The reaction mixture was partitioned between 1N aqueous HCl and ethyl acetate. The ethyl acetate phase was washed with water, then brine, dried over magnesium sulfate, and concentrated to an off-white solid. This was recrystallized from ethyl acetate/hexanes. $^1$HNMR (500 MHz, DMSO-d$_6$): δ7.70 (M, 3H), 7.73 (m, 2H), 7.89 (m, 1H), 7.93 (M, 1H), 8.19 (m, 1H), 8.32 (m, 1H), 10.60 (s, 1H).

Example 10

4-chloro-2-(2-chloro-4-nitrophenylcarbamoyl)phenyl dimethyl carbamate (Compound 23)

A suspension of 5-Chloro-N-(2-chloro-4-nitrophenyl)-2-hydroxybenzamide (238 mg, 0.728 mmol) in pyridine (5 mL) was treated with 4-dimethylaminopyridine (5 mg) and dimethyl carbamoyl chloride (0.16 mL) was introduced dropwise. The resulting suspension was warmed to reflux for three hours, then cooled to room temperature. 1N aqueous HCl (20 mL) was added, causing the product to crystallize. The crude product was collected by filtration, dried under vacuum then recrystallized from ethyl acetate to give an off-white solid. $^1$HNMR (500 MHz, DMSO-d$_6$): δ 2.845 (s, 3H, N-methyl), 2.98s (s, 3H, N-methyl), 7.329 (d, J=9 Hz, 1H, H3), 7.641 (dd, J=3, 9 Hz, 1H, H4), 7.754 (d, J=3 Hz, 1H, H6), 8.079 (d, J=9 Hz, 1H, H6'), 8.264 (dd, J=3, 9 Hz, 1H, H5'), 8.392 (d, J=3 Hz), 10.370 (s, 1H, OH).

Example 11

(R)-4-chloro-2-(2-chloro-4-nitrophenylcarbamoyl) phenyl 2-(2,2-dimethyl-5-oxo-1,3-dioxolan-4-yl) acetate (Compound 24)

A suspension of (R)-(−)-2,2-Dimethyl-5-oxo-1,3-dioxolane-4-acetic acid (Sigma-Aldrich, St. Louis, Mo.) (2.17 g, 12.46 mmol) in chloroform (24 mL) was treated with oxalyl chloride (2.11 mL, 25 mmol) and a drop of N,N-dimethylformamide was added. The progression of reaction was monitored by the observation of gas evolution by means of a bubbler. After 2 hours at room temperature, the reaction mixture was warmed to 50° C. for 2 hours, cooled to room temperature, and concentrated to remove volatiles. This residue was diluted with chloroform (10 mL) and added to a suspension of 5-Chloro-N-(2-chloro-4-nitrophenyl)-2-hydroxybenzamide (2.04 g, 6.23 mmol) in pyridine (30 mL) in which 4-dimethylaminopyride (20 mg) had been previously dissolved. The reaction mixture was stirred at room temperature for 16 h and then was partitioned between 1N aqueous HCl and ethyl acetate. The ethyl acetate solution was dried over magnesium sulfate and concentrated to a dark oil. The residue was dissolved in chloroform and placed upon a short column of silica gel (60 mm i.d.×15 mm). The product was eluted with chloroform and concentrated to an oil. The product was crystallized with a mixture of hexanes and ethyl acetate. $^1$HNMR (300 MHz, DMSO-d$_6$): δ 1.456 (s, 3H), 1.495 (s, 3H), 4.939 (m, 1H), 7.352 (d, J=9 Hz, 1H, H3), 7.730 (dd, J=3.9 Hz, 1H, H4), 7.851 (d, J=3 Hz, 1H, H6), 8.110 (d, J=9 Hz, 1H, H6'), 8.255 (dd, J=3, 9 Hz, 1H, H5'), 8.411 (d, J=3 Hz, 1H, H3'), 10.481 (s, 1H, NH).

Example 12

(S)-1-(4-chloro-2-(2-chloro-4-nitrophenylcarbamoyl) phenyl 2-methyl pyrrolidine-1,2-dicarboxylate (Compound 25)

(S)-Methyl 1-(chlorocarbonyl)pyrrolidine-2-carboxylate was prepared following the procedure disclosed in U.S. Pat. No. 4,866,087 to Greenlee et al with minor modification. A solution of 5.63 g (19.0 mmol) bis(trichloromethyl carbonate in chloroform (15 mL) was added dropwise to a solution of (S)-Methyl pyrrolidine-2-carboxylate hydrochloride (2.62 g., 15.82 mmol) and diisopropylethylamine (11.0 mL, 63.28 mmol) in chloroform (15 mL) at ice-bath temperature. After one hour, the solution was washed with 1 N aqueous HCl and water, and dried over magnesium sulfate. The dried solution was concentrated and placed on a 85 mm i.d.×35 mm column of silica gel. The product was eluted in 20 percent ethyl acetate in hexanes and concentrated to a colorless oil. This was dissolved in chloroform (10 mL) and added to a suspension of 5-Chloro-N-(2-chloro-4-nitrophenyl)-2-hydroxybenzamide (645 mg, 1.97 mmol) in pyridine (15 mL) containing 20 mg of 4-dimethylaminopyridine. After stirring for 120 hours at room temperature, the reaction solution was partitioned between 1N aqueous HCl and ethyl acetate. The ethyl acetate phase was washed with water, then brine, and dried over magnesium sulfate. Concentration afforded an off-white solid which was recrystallized from ethyl acetate/hexanes. The $^1$H NMR spectrum is complex and reveals the existence of rotational isomers due to restricted rotation about the pyrrolidine-1-carboxylate bond. $^1$HNMR (300 MHz, DMSO-$d_6$): δ 1.823-2.003 (m, 3H, pyrrolidine C4 methylene and pyrrolidine C3 syn-H), 2.213 (m, 1H, pyrrolidine C3 anti-H), 3.450 (m, 1H, pyrrolidine C5), 3.599 (m, 1H, pyrrolidine C5), 3.600 (s, 1.5H, methyl ester), 3.621 (s, 1.5H, methyl ester), 4.252 (m, 0.5H, pyrrolidine methine), 4.541 (m, 0.5H, pyrrolidine methine), 7.108 (d, J=8.5 Hz, 0.33H, H3), 7.216 (d, J=8.5 Hz, 0.33H, H3), 7.361 (d, J=9 Hz, 0.33H, H3), 7.545 (m, 0.33H, H4), 7.665 (m, 0.66H, H4), 7.763 (m, 0.66H, H6), 7.974 (m, 0.33H, H6), 8.133 (m, 0.66H, H6'), 8.287 (m, 1H, H5'), 8.302 (m, 0.33H, H3'), 8.539 (m, 0.33H, H3'), 8.446 (m, 0.33H, H3'), 8.822 (d, J=9.5 Hz, 0.33H, H6'), 10.313 (s, 0.33H, NH), 10.385 (s, 0.33H, NH), 11.367 (br s, 0.17H, NH), 12.519 (br s, 0.17H, NH).

Example 13

(S)-2-tert-butyl 1-(4-chloro-2-(2-chloro-4-nitrophenylcarbamoyl)phenyl pyrrolidine-1,2-dicarboxylate (Compound 26)

(S)-tert-butyl 1-(chlorocarbonyl)pyrrolidine-2-carboxylate was prepared following the procedure disclosed in U.S. Pat. No. 4,866,087 to Greenlee et al with minor modification. A solution of 1.06 g (6.19 mmol) (S)-2-tert-butyl pyrrolidine-2-carboxylate and diisopropylethylamine (3.2 mL, 18.57 mmol) in dichloromethane (5.0 mL) was introduced dropwise into a solution of 1.84 g (6.19 mmol) bis(trichloromethyl)carbonate in dichloromethane (5.0 mL) at ice-bath temperature. The mixture was allowed to warm to room temperature and was stirred for one hour. The reaction mixture was washed with 1N aqueous HCl, dried over magnesium sulfate, and concentrated to an oil. The residue was dissolved in chloroform (5.0 mL) and added dropwise to a suspension of 5-Chloro-N-(2-chloro-4-nitrophenyl)-2-hydroxybenzamide (1.82 g, 5.57 mmol) in pyridine (25 mL) containing 20 mg 4-dimethylaminopyridine. The reaction mixture was stirred at room temperature for 72 hours, then partitioned between ethyl acetate and 1N aqueous HCl, dried over magnesium sulfate, and concentrated to a solid. The product was isolated using silica gel chromatography with 3 ethyl acetate:7 hexanes as elution solvent. The product was recrystallized from ethyl acetate/hexanes. $^1$H NMR reveals the existence of approximately a 1:1 ratio of rotational isomers. $^1$H NMR (CDCl$_3$): δ1.331 (s, 4.5H, tert-butyl ester), 1.369 (s, 4.5H, tert-butyl ester), 1.833 (m, 3H, pyrrolidine C4 methylene and pyrrolidine C3 syn-H), 2.181 (m, 1H, pyrrolidine C3 anti-H), 3.500 (m, 2H, pyrrolidine C5 methylene), 4.113 (m, 0.5H, pyrrolidine methine), 4.362 (m, 0.5H, pyrrolidine methine), 7.158 (d, J=9 Hz, 0.5H, H3), 7.334 (d, J=9 Hz, 0.5H, H3), 7.661 (m, 1H, H4), 7.762 (m, 1H, H6), 8.131 (m, 1H, H6'), 8.312 (m, 1H, H5'), 8.388 (m, 1H, H3'), 10.274 (s, 0.5H, NH), 10.347 (s, 0.5H, NH).

Example 14

(S)-1-((4-chloro-2-(2-chloro-4-nitrophenylcarbamoyl)carbonyl)pyrrolidine-2-carboxylic acid (Compound 27)

A solution of 269 mg (S)-2-tert-butyl 1-(4-chloro-2-(2-chloro-4-nitrophenylcarbamoyl)phenyl pyrrolidine-1,2-dicarboxylate in chloroform (4.0 mL) was treated with water (0.2 mL) and trifluoroacetic acid (4.0 mL) was added. The reaction mixture was stirred at room temperature for 1.5 hours then concentrated. The residue was taken up in chloroform (15 mL) and concentrated. The residue was dissolved in ethyl acetate (10 mL) and concentrated to provide a white solid. $^1$H NMR reveals the existence of approximately a 1:1 ratio of rotational isomers. $^1$H NMR (CDCl$_3$): δ2.043 (m, 2H, pyrrolidine C4 methylene), 2.278 (m, 2H, pyrrolidine C3 methylene), 3.685 (m, 2H, pyrrolidine c5 methylene), 4.414 (m, 0.5H, pyrrolidine methine), 4.593 (m, 0.5H, pyrrolidine methine), 7.109 (d, J=9 Hz, 0.5H, H3), 7.201 (d, J=9 Hz, 0.5H, H3), 7.492 (m, 1H, H4), 7.841 (m, 1H, H6), 8.196 (m, 1H, H6'), 8.299 (m, 1H, H5'), 8.760 (m, 1H, H3'), 8.852 (m, 1H, NH).

Example 15

Cells stably transfected with mGlu1 or mGlu5 were grown 18 hours prior to the test in culture medium containing 600 ng/ml doxycycline, then were detached by gentle flushing with PBS-EDTA, recovered by centrifugation and resuspended in "assay buffer" (HBSS, 2.1 mM CaCl2, 3 μg/ml GPT (Glutamate-Pyruvate transaminase), 4 mM MEM Sodium Pyruvate, 0.1% BSA, protease free). Cells were incubated at room temperature for at least 4 h with coelenterazine-h. Dose response curves were performed using mGluR1 cells with the orthosteric agonist glutamate and negative allosteric modulator JNJ16259685. Dose response curves were performed using mGluR5 cells with the orthosteric agonist glutamate and negative allosteric modulator MPEP. For agonist testing, 30 μl of cell suspension were mixed with 30 μl of test compound or reference agonist in a 384-well plate. The resulting emission of light was recorded using the Hamamatsu Functional Drug Screening System 6000 (FDSS 6000). For negative allosteric modulator testing, 60 μl of the resulting cell suspension containing the test compound was mixed with 30 μl of the reference agonist at EC80 following an incubation of 3 min after the first injection. The resulting emission of light was recorded using FDSS 6000. To standardize the emission of recorded light (determination of the "100% signal") across plates and across different experiments, some of the wells contained 100 μM digitonin or a concentration of reference agonist equivalent to the EC100. Plates also contained the reference agonist at a concentration equivalent to the EC80 obtained during the test validation. Negative allosteric modulator activity of test compound was expressed as a percentage of the stimulation of reference agonist activity at its EC80 concentration.

Example 16

A total of 50, male Sprague-Dawley rats (125-150 g weight) were received from Ace Animals. Animals were housed in cages which conform to the size recommendations in the most recent *NIH Guide for the Care and Use of Laboratory Animals*. The animal room was temperature controlled and had a 12-hour light/dark cycle. The animals were fed Purina Rodent Chow #5012. The animals were acclimated to the facility for 7 days prior to the study. A pre-operative baseline paw withdrawal measure was collected for all rats. All rats underwent partial sciatic nerve ligation or a sham surgery (allocated randomly), and had a three week recovery period. After recovery, a pre-dosing baseline paw withdrawal threshold was collected for all rats. The results of this measure was used to assign rats to treatment groups in a stratified random fashion. Rats were lightly anesthetized and treated with test article or vehicle. Paw withdrawal thresholds were determined at one, three, five, and 24 hours post dosing. The sciatic nerve was partially ligated as a model of neuropathic pain (Y. Shir & Z. Seltzer, 1990, Neurosci. Lett., 115:62-7). Briefly, under gas anesthesia, the skin and muscles of the thigh were reflected to expose the sciatic nerve. About one third to one half of the cross-sectional area of the nerve was tightly ligated using a 7-0 nylon suture. The incision was closed in layers (suture for muscle, surgical adhesive for skin). Test article or vehicle was administered by transcutaneous injection (C. Mestre et al., 1994, J. Pharm. Tox. Meth., 32:197-200). Briefly, the rat was lightly anesthetized and placed to flex the lower lumbar vertebrae. After palpating the vertebral processes, a 26 gauge needle was inserted through a vertebral interspace. The presence of a tail flick was considered validation of the needle placement; the solution was then injected. Paw withdrawal thresholds were assessed using a paw pressure device (L. O. Randall & J. J. Selitto, 1957, *Arch. Int. Pharmacodyn.*, 111:409-19). The behavioral endpoint was defined as paw withdrawal. Data was analyzed by two-way analysis of variance (repeated measures) with Bonferroni tests at individual time points. Paw withdrawal threshold raw values were used for the analysis, and each route of administration was analyzed separately. Vehicle-treated groups were used as the statistical comparison groups. All groups began the study with normal paw withdrawal thresholds (FIG. 1, Pre-Sx time point). Partial sciatic nerve ligation (PSN) surgery decreased withdrawal thresholds compared to sham (control) surgery. This hyperalgesia is characteristic of the model. Sham/vehicle and PSN/vehicle groups maintained relatively stable average thresholds, despite relatively small group sizes (PSN/vehicle, n=7; all other groups, n=6). The differences between sham/vehicle and PSN/vehicle groups were statistically significant at all post-surgery time points. Gabapentin was effective in reversing hyperalgesia. The reversal of hyperalgesia seen with gabapentin is consistent with that seen after treatment with compounds known to have clinical activity against neuropathic pain.

Each and every patent, published patent application, and other reference cited above is incorporated herein in its entirety.

Those with skill in the art will recognize, or be able to ascertain using no more than routine experimentation, many equivalents to the specific embodiments of the invention described herein. Such equivalents are within the scope of the present invention and are intended to be encompassed by the following claims.

We claim:

1. A method of treating pain by administering a noncompetitive Group 1 mGluR negative allosteric modulator compound, its pharmaceutically acceptable salts, prodrugs, or pharmaceutically acceptable salts of its prodrugs to an animal wherein said compound has the formula:

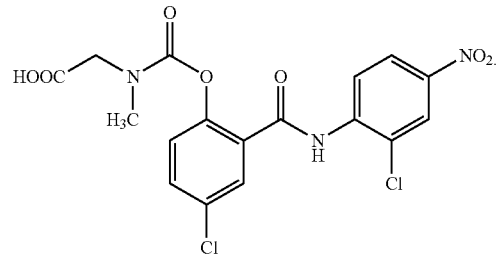 [SMILES: CN(CC(=O)O)C(=O)Oc1ccc(Cl)cc1C(=O)Nc1ccc([N+](=O)[O-])cc1Cl]

2. The method of claim 1 wherein said pain is acute or chronic pain.

3. The method of claim 1 wherein said pain is selected from the group consisting of bone and joint pain, repetitive motion pain, dental pain, cancer pain, myofacial pain, perioperative pain, chronic pain, neuropathic pain, post-traumatic pain, trigeminal neuralgia, migraine and migraine headache, neuropathic pain, diabetic neuropathy, entrapment neuropathy, phantom pain, thalamic pain after stroke, post-herpetic neuralgia, atypical facial neuralgia pain after tooth extraction, pain from spinal cord injury, trigeminal neuralgia and cancer pain resistant to narcotic analgesics.

4. The method of claim 1 wherein said pain is diabetic neuropathy.

5. The method of claim 1 wherein said pain is neuropathic pain.

* * * * *